US012765905B2

(12) United States Patent
Graul et al.

(10) Patent No.: US 12,765,905 B2
(45) Date of Patent: Oct. 20, 2026

(54) AUGMENT DELIVERY INSTRUMENT AND METHOD OF USE

(71) Applicant: Stryker Corporation, Kalamazoo, MI (US)

(72) Inventors: Jeremy Ming Graul, Denver, CO (US); Mark Larson, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 105 days.

(21) Appl. No.: 18/755,914

(22) Filed: Jun. 27, 2024

(65) Prior Publication Data

US 2025/0000511 A1 Jan. 2, 2025

Related U.S. Application Data

(60) Provisional application No. 63/524,103, filed on Jun. 29, 2023.

(51) Int. Cl.

*A61B 17/28* (2006.01)
*A61B 17/00* (2006.01)
*A61B 17/04* (2006.01)

(52) U.S. Cl.

CPC .... *A61B 17/28* (2013.01); *A61B 2017/00238* (2013.01); *A61B 2017/0409* (2013.01)

(58) Field of Classification Search

CPC .......... A61B 17/28; A61B 2017/00238; A61B 2017/0409; A61B 17/29; A61B 17/282; A61B 17/2816; A61B 17/2812; A61B 17/2804; A61B 2017/2829; A61B 2017/2825; A61B 2017/2808; A61F 2002/0072; A61F 2/0805

USPC .......................................................... 606/207

See application file for complete search history.

(56) References Cited

U.S. PATENT DOCUMENTS 4,374,523 A * 2/1983 Yoon ....................... A61F 6/208 606/140
4,393,872 A * 7/1983 Reznik ................... A61B 17/29 604/151
5,284,162 A * 2/1994 Wilk ...................... A61B 17/29 606/205
5,370,650 A 12/1994 Tovey et al.
5,383,477 A 1/1995 DeMatteis
5,803,902 A 9/1998 Sienkiewicz et al.
6,428,546 B1 8/2002 Cancel et al.
6,478,803 B1 11/2002 Kapec et al.

(Continued)

FOREIGN PATENT DOCUMENTS

WO 2024/054550 A2 3/2024

*Primary Examiner* — Dianne Dornbusch
(74) *Attorney, Agent, or Firm* — Foley & Lardner LLP

(57) ABSTRACT

An implant delivery instrument may include a base support with a shaft and a jaw extending therefrom and a closed loop member including first and second lateral strips connected by an end strip attached to the jaw with the jaw extending into an opening of the closed loop. The closed loop may be deformable to temporarily create a gap between ends of the closed loop and jaw so that an implant may be inserted therebetween. The instrument may also include an elongate housing slidably disposed over the shaft, the elongate housing being movable between a retracted position exposing the jaw and the closed loop and a deployed position enclosing the jaw and the closed loop.

20 Claims, 23 Drawing Sheets

(56) References Cited

U.S. PATENT DOCUMENTS

| | | | |
|---|---|---|---|
| 6,522,932 | B1 | 2/2003 | Kuzma et al. |
| 7,794,484 | B2 | 9/2010 | Stone et al. |
| 7,819,797 | B2 | 10/2010 | Vanden Hoek et al. |
| 7,819,880 | B2 | 10/2010 | Zannis et al. |
| 7,846,171 | B2 | 12/2010 | Kullas et al. |
| 7,981,024 | B2 | 7/2011 | Levy |
| 8,012,174 | B2 | 9/2011 | ElAttrache et al. |
| 8,097,008 | B2 | 1/2012 | Henderson |
| 8,221,440 | B2 | 7/2012 | Kullas et al. |
| 8,241,298 | B2 | 8/2012 | Sengun et al. |
| 8,317,808 | B2 | 11/2012 | Levin et al. |
| 8,460,321 | B2 | 6/2013 | Newell et al. |
| 8,465,516 | B2 | 6/2013 | Pavcnik et al. |
| 8,517,914 | B2 | 8/2013 | Anderson et al. |
| 8,579,989 | B2 | 11/2013 | Leahy |
| 8,585,773 | B1 | 11/2013 | Kucklick |
| 8,668,718 | B2 | 3/2014 | Euteneuer et al. |
| 8,673,021 | B2 | 3/2014 | Orr et al. |
| 8,753,359 | B2 | 6/2014 | Levin et al. |
| 8,753,361 | B2 | 6/2014 | Abuzaina et al. |
| 8,758,373 | B2 | 6/2014 | Levin et al. |
| 8,763,878 | B2 | 7/2014 | Euteneuer et al. |
| 8,808,314 | B2 | 8/2014 | Levin et al. |
| 8,821,507 | B2 | 9/2014 | Axelson, Jr. et al. |
| 8,821,537 | B2 | 9/2014 | Euteneuer et al. |
| 8,840,642 | B2 | 9/2014 | Euteneuer et al. |
| 8,845,648 | B2 | 9/2014 | Guzman et al. |
| 8,864,780 | B2 | 10/2014 | Euteneuer et al. |
| 8,888,811 | B2 | 11/2014 | Levin et al. |
| 8,906,045 | B2 | 12/2014 | Levin et al. |
| 8,920,302 | B2 | 12/2014 | Levy |
| 8,920,445 | B2 | 12/2014 | Sholev |
| 8,920,464 | B2 | 12/2014 | Euteneuer et al. |
| 8,932,201 | B2 | 1/2015 | Montpetit et al. |
| 9,005,224 | B2 | 4/2015 | Euteneuer et al. |
| 9,005,241 | B2 | 4/2015 | Levin et al. |
| 9,027,819 | B2 | 5/2015 | Euteneuer et al. |
| 9,034,002 | B2 | 5/2015 | Bolduc et al. |
| 9,044,235 | B2 | 6/2015 | Iceman et al. |
| 9,095,337 | B2 | 8/2015 | Euteneuer et al. |
| 9,101,460 | B2 | 8/2015 | Euteneuer et al. |
| 9,107,726 | B2 | 8/2015 | Levin et al. |
| 9,113,977 | B2 | 8/2015 | Euteneuer et al. |
| 9,149,369 | B2 | 10/2015 | Sengun et al. |
| 9,179,910 | B2 | 11/2015 | Euteneuer et al. |
| 9,179,961 | B2 | 11/2015 | Euteneuer et al. |
| 9,198,751 | B2 | 12/2015 | Euteneuer et al. |
| 9,204,940 | B2 | 12/2015 | Euteneuer et al. |
| 9,226,828 | B2 | 1/2016 | Bonutti |
| 9,259,220 | B2 | 2/2016 | Euteneuer et al. |
| 9,271,766 | B2 | 3/2016 | Bonutti |
| 9,301,826 | B2 | 4/2016 | Palmer et al. |
| 9,314,314 | B2 | 4/2016 | Euteneuer et al. |
| 9,314,331 | B2 | 4/2016 | Euteneuer et al. |
| 9,393,002 | B2 | 7/2016 | Iceman et al. |
| 9,393,093 | B2 | 7/2016 | Iceman et al. |
| 9,398,944 | B2 | 7/2016 | Palmer et al. |
| 9,414,738 | B2 | 8/2016 | Huszar et al. |
| 9,545,268 | B2 | 1/2017 | Bonutti |
| 9,579,129 | B2 | 2/2017 | Bonutti |
| 9,615,907 | B2 | 4/2017 | Horton |
| 9,675,346 | B2 | 6/2017 | Euteneuer et al. |
| 9,713,418 | B2 | 7/2017 | Huszar et al. |
| 9,743,970 | B2 | 8/2017 | Euteneuer et al. |
| 9,820,842 | B2 | 11/2017 | Shandas et al. |
| 9,826,972 | B2 | 11/2017 | Ranucci et al. |
| 9,827,111 | B2 | 11/2017 | Orr et al. |
| 9,833,240 | B2 | 12/2017 | Glick et al. |
| 9,848,999 | B2 | 12/2017 | Sengun et al. |
| 9,867,706 | B2 | 1/2018 | Bonutti |
| 9,878,141 | B2 | 1/2018 | Kucklick |
| 9,931,119 | B2 | 4/2018 | Euteneuer et al. |
| 9,974,636 | B2 | 5/2018 | Montpetit et al. |
| 9,974,638 | B2 | 5/2018 | Zoll et al. |
| 9,993,324 | B2 | 6/2018 | Sholev |
| 9,999,424 | B2 | 6/2018 | Levin et al. |
| 9,999,449 | B2 | 6/2018 | Bonutti |
| 10,034,733 | B2 | 7/2018 | Anderson et al. |
| 10,034,736 | B2 | 7/2018 | Blackburn et al. |
| 10,085,785 | B2 | 10/2018 | Euteneuer et al. |
| 10,117,734 | B2 | 11/2018 | Guo et al. |
| 10,123,796 | B2 | 11/2018 | Westling et al. |
| 10,159,554 | B2 | 12/2018 | Iceman et al. |
| 10,182,898 | B2 | 1/2019 | Iceman et al. |
| 10,195,016 | B2 | 2/2019 | Euteneuer et al. |
| 10,226,325 | B2 | 3/2019 | Euteneuer et al. |
| 10,238,378 | B2 | 3/2019 | Bonutti et al. |
| 10,245,138 | B2 | 4/2019 | Euteneuer et al. |
| 10,258,459 | B2 | 4/2019 | Zenz-Olson |
| 10,278,801 | B2 | 5/2019 | Kucklick |
| 10,307,238 | B2 | 6/2019 | Kucklick |
| 10,314,689 | B2 | 6/2019 | Zenz-Olson et al. |
| 10,335,256 | B2 | 7/2019 | Montpetit et al. |
| 10,398,579 | B2 | 9/2019 | Faizer |
| 10,413,397 | B2 | 9/2019 | Euteneuer et al. |
| 10,426,464 | B2 | 10/2019 | Euteneuer et al. |
| 10,449,031 | B2 | 10/2019 | Euteneuer et al. |
| 10,568,622 | B2 | 2/2020 | Euteneuer et al. |
| 10,624,730 | B2 | 4/2020 | Shandas et al. |
| 10,653,415 | B2 | 5/2020 | Euteneuer et al. |
| 10,675,016 | B2 | 6/2020 | Coleman |
| 10,695,155 | B2 | 6/2020 | Levin et al. |
| 10,751,156 | B2 | 8/2020 | Sholev et al. |
| 10,765,423 | B2 | 9/2020 | Coleman |
| 10,786,232 | B2 | 9/2020 | Murray |
| 10,806,565 | B2 | 10/2020 | Euteneuer et al. |
| 10,813,764 | B2 | 10/2020 | Bonutti |
| 10,820,981 | B2 | 11/2020 | Ravenscroft et al. |
| 10,821,005 | B2 | 11/2020 | Sengun et al. |
| 10,835,235 | B2 | 11/2020 | Coleman |
| 10,835,368 | B2 | 11/2020 | Zenz-Olson et al. |
| 10,874,503 | B2 | 12/2020 | Zenz-Olson et al. |
| 10,881,441 | B2 | 1/2021 | Euteneuer et al. |
| 10,898,228 | B2 | 1/2021 | Zenz-Olson et al. |
| 10,912,579 | B2 | 2/2021 | Kucklick |
| 10,925,638 | B2 | 2/2021 | Park et al. |
| 10,952,783 | B2 | 3/2021 | Euteneuer et al. |
| 10,987,210 | B2 | 4/2021 | Zenz-Olson et al. |
| 10,993,795 | B2 | 5/2021 | Guo et al. |
| 11,051,808 | B2 | 7/2021 | Euteneuer et al. |
| 11,051,932 | B2 | 7/2021 | Euteneuer et al. |
| 11,076,851 | B2 | 8/2021 | Westling et al. |
| 11,116,623 | B2 | 9/2021 | Euteneuer et al. |
| 11,185,402 | B2 | 11/2021 | Kucklick |
| 11,207,165 | B2 | 12/2021 | Montpetit et al. |
| 11,213,378 | B2 | 1/2022 | Fischer |
| 11,229,509 | B2 | 1/2022 | Kucklick |
| 11,259,939 | B2 | 3/2022 | Churchill et al. |
| 11,331,180 | B2 | 5/2022 | Zenz-Olson |
| 11,373,554 | B2 | 6/2022 | Myers et al. |
| 11,375,996 | B2 | 7/2022 | Coleman |
| 11,413,082 | B2 | 8/2022 | Euteneuer et al. |
| 11,413,133 | B2 | 8/2022 | Euteneuer et al. |
| 11,426,156 | B2 | 8/2022 | Coleman |
| 11,457,958 | B2 | 10/2022 | Bonutti |
| 11,510,702 | B2 | 11/2022 | Zenz-Olson et al. |
| 11,554,028 | B2 | 1/2023 | Sengun et al. |
| 11,579,666 | B2 | 2/2023 | Wang et al. |
| 11,648,001 | B2 | 5/2023 | Fischer et al. |
| 11,672,520 | B2 | 6/2023 | Lamson et al. |
| 11,723,706 | B2 | 8/2023 | Euteneuer et al. |
| 11,771,416 | B2 | 10/2023 | Dooney, Jr. et al. |
| 11,779,371 | B1 | 10/2023 | Levy et al. |
| 11,806,223 | B2 | 11/2023 | Sholev et al. |
| 11,850,167 | B2 | 12/2023 | Churchill et al. |
| 11,872,117 | B2 | 1/2024 | Kucklick |
| 11,877,743 | B2 | 1/2024 | Fischer et al. |
| 11,918,448 | B2 | 3/2024 | Kucklick |
| 11,957,566 | B2 | 4/2024 | Bonner et al. |
| 11,992,396 | B2 | 5/2024 | Kucklick |
| 2007/0112361 | A1 | 5/2007 | Schonholz et al. |
| 2007/0185506 | A1 | 8/2007 | Jackson |
| 2009/0156997 | A1 | 6/2009 | Trenhaile |

(56) References Cited

U.S. PATENT DOCUMENTS

| | | | |
|---|---|---|---|
| 2020/0214696 | A1 | 7/2020 | Harris et al. |
| 2023/0263615 | A1 | 8/2023 | Grabinsky et al. |
| 2023/0346412 | A1 | 11/2023 | Kucklick |

* cited by examiner

AUGMENT DELIVERY INSTRUMENT AND METHOD OF USE

CROSS-REFERENCE TO RELATED APPLICATION

This application claims the benefit of U.S. Provisional Pat. App. No. 63/524,103 filed Jun. 29, 2023, the disclosure of which is hereby incorporated by reference herein in its entirety.

BACKGROUND

Joints of the human body may be susceptible to damage or injury due to excessive wear through intensive activity or through a long period of expected wear, among other reasons. One joint particularly susceptible to injury is the shoulder, where the tendons or muscles of the rotator cuff may tear. While it is desirable to conduct a procedure to repair the rotator cuff that is minimally invasive, such procedures have been difficult to execute due to the limited space available to deliver an implant to the repair site in a patient. Additionally, even when an implant is successfully placed at the repair site, it is often misshapen and therefore difficult to properly attach the implant to the tissue.

Accordingly, a need exists for improved instrumentation for the delivery and placement of implants to repair tissue in human joints such as the rotator cuff in the shoulder.

BRIEF SUMMARY

In one aspect, the present disclosure relates to an implant delivery instrument, also referred to as a delivery instrument. In a first embodiment, an implant delivery instrument includes a base support, a first actuation assembly and a second actuation assembly. The base support includes a base shaft extending along a central longitudinal axis in a proximal-distal direction, a jaw extending distally from the base shaft and a central body extending distally from the base shaft. The first actuation assembly includes a first lateral wing extending distally along a first side of the central longitudinal axis to a distal portion of the central body. The second actuation assembly includes an elongate housing with a lumen therethrough, the elongate housing disposed such that the base support and the first actuation assembly pass through the lumen and the elongate housing is slidable relative to the base support between an unlocked position and a locked position. The elongate housing may be configured so that when the elongate housing is in the unlocked position, at least one of the central body and the jaw is biased such that the distal portion of the central body is a first distance from the jaw. The elongate housing may also be configured so that when the elongate housing is in the locked position, the distal portion of the central body is a second distance from the jaw, the second distance being less than the first distance. Further, the first lateral wing is actuatable independently of the elongate housing to control displacement of the first lateral wing relative to the central body.

In some examples of the first embodiment, the implant delivery instrument may also include a third actuation assembly. The third actuation assembly may include an outer shaft. The outer shaft may be disposed over the base support, the first actuation assembly and the second actuation assembly, the outer shaft being slidable along the central longitudinal axis in a proximal-distal direction between a retracted position and an extended position, wherein the jaw and the central body are at least partially exposed in the retracted position and the jaw and the central body are entirely within a lumen of the outer shaft in the extended position.

In some examples of the first embodiment, the implant delivery instrument may be configured such that actuation of the first lateral wing causes an extent of buckling in a portion of the first lateral wing to change relative to the central body. In further examples of this configuration, the portion of the first lateral wing subject to buckling may be displaced in a direction transverse to a direction of displacement of at least one of the central body and the jaw when the elongate housing is moved between the unlocked and locked positions.

In some examples of the first embodiment, when the elongate housing is in the unlocked position, a length of the central body may be at an angle relative to a length of the elongate jaw. In other examples of the first embodiment, when the elongate housing is in the unlocked position, a length of the central body may be parallel to a length of the elongate jaw.

In some examples of the first embodiment, the central body of the implant delivery instrument may include a closed loop of material. The closed loop of material may include a pair of elongate central strips oriented in alignment with the central longitudinal axis, the pair of elongate central strips being joined together by at least one lateral strip. In some of these examples, the lateral strip may be located proximate the distal portion of the central body.

In some examples of the first embodiment, the first lateral wing may be attached to the central body via a pin connection such that the first lateral wing is rotatable about the pin connection. In further examples, the implant delivery instrument may also include a second lateral wing. In such examples, the second lateral wing may extend distally along a second side of the central longitudinal axis to the distal portion of the central body. In this configuration, the second side and the first side are on opposite sides of the central longitudinal axis. Additionally, the second lateral wing may be actuatable together with the first lateral wing to control displacement of the first and second lateral wings relative to the central body.

In other examples of the first embodiment, the implant delivery instrument may form part of a kit. In some of these examples, the kit may include an implant delivery instrument and an implant. The implant may be adapted to be received in between the central body and the jaw when the elongate housing is in the unlocked position.

In a second embodiment, an implant delivery instrument includes a central shaft, a first gripper, a second gripper and an elongate housing. The central shaft is oriented along a central longitudinal axis of the implant delivery instrument. The first gripper is attached to a distal end portion of the central shaft, the first gripper including a jaw extending distally from the central shaft. The second gripper is attached to and extends distally from one of the distal end portion of the central shaft and the first gripper. The second gripper includes first and second lateral strips that extend distally from a base and are spaced apart from one another in a lateral direction so as to define a central opening therebetween. The jaw of the first gripper is positioned so that it extends to a tip such that at least a portion of the jaw including the tip passes through the central opening of the second gripper. The first and second gripper are configured such that an implant is receivable in between the second gripper and the jaw of the first gripper by holding one of the second gripper and the jaw to create a space between the second gripper and the jaw to receive the implant. The elongate housing includes a lumen therethrough, the elongate housing being disposed over the central shaft such that the central shaft passes through the lumen. The elongate housing is slidable along the central longitudinal axis such that a greater portion of the first and second grippers is exposed when the elongate housing is in a retracted position than when the elongate housing is in an extended position.

In some examples, the second gripper of the implant delivery instrument of the second embodiment may include an end strip connecting the distal ends of the first and second lateral strips such that a closed loop is defined by the end strip, the first and second lateral strips, and the base encircling the central opening.

In some examples, the implant delivery instrument of the second embodiment may be configured such that the first and second lateral strips and the end strip are not in contact with the jaw irrespective of bending of the second gripper to facilitate insertion of an implant in between the second gripper and the jaw.

In some examples, the second gripper of the implant delivery instrument of the second embodiment may be biased relative to the jaw such that the portion of the jaw extends into the central opening of the second gripper.

In some examples, the first and second lateral strips of the implant delivery instrument may be flexible and sized such that when the elongate housing is slid into the extended position over the first and second lateral strips, the first and second lateral strips bend inward to pass into the lumen of the elongate housing.

In some examples, the elongate housing of the implant delivery instrument of the second embodiment may have an inner diameter greater than a maximum width dimension of the second gripper. In certain of these examples, the first lateral strip may include a first branch that extends from a first location on the first lateral strip at a first acute angle relative to a length direction of the first lateral strip and the second lateral strip may include a second branch that extends from a second location on the second lateral strip at a second acute angle relative to a length direction of the second lateral strip. The first and second locations may be different distances from the distal end of the central shaft, and the first and second locations may be spaced apart from the end strip. In certain of these examples, the second gripper may include an attachment point above the first gripper for attachment to the first gripper and the first and second branches may be biased away from a plane through the lateral strips on a side of the plane including a base of the jaw.

In some examples of the implant delivery instrument of the second embodiment, the closed loop defined by the second gripper is a first elongate closed loop overlay. Additionally, the second gripper may also include a second elongate closed loop overlay such that the first elongate closed loop overlay and the second elongate closed loop overlay are both attached onto a base of the first distal gripper and the jaw passes through an opening inside of the first and second elongate closed loop overlays. In certain of these examples, the second elongate closed loop overlay may include an extension tab at a distal end of the second elongate closed loop overlay, the extension tab being engaged to the first elongate closed loop overlay. In certain of these examples, the first elongate closed loop overlay may have a first modulus of elasticity and the second elongate closed loop overlay may have a second modulus of elasticity less than the first modulus of elasticity. In certain of these examples, the combined first and second elongate closed loop overlays may be monolithic.

In some examples, the second gripper of the implant delivery instrument of the second embodiment may include a first wing extending from the base of the elongate closed loop overlay to a distal end of the elongate closed loop overlay on a first side of the elongate closed loop overlay and a second wing extending from the base of the elongate closed loop overlay to the distal end of the elongate closed loop overlay on a second side of the elongate closed loop, the second side being opposite the first side. In certain of these examples, the first wing and the second wing may be biased away from a plane passing through the first lateral strip, the second lateral strip and the end strip of the elongate closed loop overlay.

In some examples of the implant delivery instrument of the second embodiment, the first gripper may be made of polymeric material and the second gripper may be made of a metallic material. In other examples of the second embodiment, the implant delivery instrument may include a funnel adapted to snap onto the elongate housing, the funnel including an opening on one side so that the first and second grippers are accessible when the funnel is attached to the elongate housing and the elongate housing is in the retracted position. In some examples, the elongate housing of the implant delivery instrument of the second embodiment may be a tube.

In a third embodiment, an implant delivery instrument includes an inner shaft, a bushing, a clamp, a jaw and a cannulated outer shaft. The bushing is slidably disposed over the inner shaft such that the bushing is axially translatable along a central longitudinal axis of the inner shaft. The clamp extends distally from a distal portion of the inner shaft and the jaw also extends distally from the distal portion. The cannulated outer shaft is disposed over the inner shaft and the bushing such that the cannulated outer shaft is axially translatable along the central longitudinal axis. The bushing is translatable between an unlocked position where the clamp is spaced apart from the jaw by a first distance and a locked position where the clamp is spaced apart from the jaw by a second distance less than the first distance. The cannulated outer shaft is translatable between a retracted position where the clamp has a first maximum lateral dimension and an extended position where the clamp has a second maximum lateral dimension less than the first maximum lateral dimension.

In some examples, the clamp of the implant delivery instrument of the third embodiment may include three prongs arranged to pass through a first plane. In certain of these examples, when the cannulated outer shaft is in the retracted position, the three prongs may be spaced part from each other by a third maximum lateral dimension and when the cannulated outer shaft is in the extended position, the three prongs may be spaced apart from each other by a fourth maximum lateral dimension less than the third maximum lateral dimension. In some examples of the third embodiment, the clamp may include a plurality of prongs. In some of the examples where the clamp includes a plurality of prongs, the implant delivery instrument may include an actuation mechanism that is configured to control a spacing of the plurality of prongs while the cannulated outer shaft is in the retracted position. In further examples of the third embodiment, the implant delivery instrument may include a first actuation mechanism that is configured to axially translate the bushing and a second actuation mechanism that is configured to axially translate the cannulated outer shaft.

In some examples, the jaw of the implant delivery instrument of the third embodiment may be a single jaw that is immovable with respect to the inner shaft.

In some examples, the implant delivery instrument of the third embodiment may be part of a kit. The kit may include the implant delivery instrument and an implant adapted for receipt in between the clamp and the jaw.

In another aspect, the present disclosure relates to an implant delivery system. In a first embodiment, an implant delivery system includes an implant and an implant delivery instrument. The implant delivery instrument includes an inner shaft, a clamp, a jaw, a bushing and a cannulated outer shaft. The bushing is slidably disposed over the inner shaft such that the bushing is axially translatable along a central longitudinal axis of the inner shaft. The clamp extends distally from a distal portion of the inner shaft, and the jaw also extends distally from the distal portion of the inner shaft. The cannulated outer shaft is disposed over the inner shaft and the bushing such that the cannulated outer shaft is axially translatable along the central longitudinal axis. The bushing is translatable between an unlocked position where the clamp is spaced apart from the jaw by a first distance and a locked position where the clamp is spaced apart from the jaw by a second distance less than the first distance. The cannulated outer shaft is translatable between a retracted position where the clamp has a first maximum lateral dimension and an extended position where the clamp has a second maximum lateral dimension less than the first maximum lateral dimension.

In some examples of the first embodiment of the implant delivery system, the clamp may include a plurality of prongs. In a subset of these examples, the implant delivery instrument is configured such that when the cannulated outer shaft is in the retracted position, the plurality of prongs are spaced part from each other by a third maximum lateral dimension and when the cannulated outer shaft is in the extended position, the plurality of prongs are spaced apart from each other by a fourth maximum lateral dimension less than the third maximum lateral dimension. In some examples of the first embodiment, the jaw may be a single jaw that is immovable with respect to the inner shaft. In further examples of the first embodiment, when the cannulated outer shaft translates from the retracted to the extended position, a width of the jaw remains unchanged. Further, in some examples of the first embodiment, at least one of the clamp and the jaw may include gripping protrusions.

In another aspect, the present disclosure relates to a method of delivering an implant to a surgical site using an implant delivery instrument. In a first embodiment of the method, the method may include one or more of the following steps: advancing an implant delivery instrument holding an implant to a tissue location in a patient; sliding the outer housing proximally to expose the jaw and the central body; actuating the lateral wing to cause at least a portion of the lateral wing to buckle outward from the central body, thereby at least partially flattening a surface of the implant; sliding the elongate housing proximally to cause the central body to move apart from the jaw; and withdrawing the implant delivery instrument from the tissue location. The implant delivery instrument used in the method may include: a base shaft extending along a central longitudinal axis in a proximal-distal direction, the base shaft including a jaw and a central body extending from a distal end thereof; a first actuation assembly including a lateral wing operatively connected to the central body, the central body being aligned with the central longitudinal axis; a second actuation assembly including an elongate housing with a lumen therethrough, the base shaft being disposed within the lumen and the elongate housing being slidable along the base shaft; and a third actuation assembly including an outer housing, the outer housing being slidably disposed over the base shaft.

In some examples of the first method embodiment, the method may include anchoring the implant to a portion of tissue at the tissue location. In some examples, the method may include, prior to the advancing step, one or more of the following additional steps: sliding the elongate housing proximally to expose the jaw and the central body; placing the implant in between the central body and the elongate jaw; sliding the elongate housing distally such that the jaw and the central body apply pressure to the implant from opposite sides of the implant.

In a second embodiment of the method, the method of delivering an implant into a patient may include: delivering an implant delivery instrument with an implant attached thereto to a target tissue location in a patient; sliding the cannulated outer shaft toward the proximal end of the inner shaft to a retracted position to expose the clamp, the clamp expanding in overall width upon exposure from the cannulated outer shaft; sliding the bushing toward a proximal end of the inner shaft to an unlocked position such that a distance between the clamp and the jaw increases; and withdrawing the implant delivery instrument from the target tissue location leaving the implant at the target tissue location. The implant delivery instrument of this embodiment may include: an inner shaft including a distal portion; a bushing slidably disposed over the inner shaft such that the bushing is axially translatable along a central longitudinal axis of the inner shaft; a clamp extending distally from the distal portion and a jaw extending distally from the distal portion; and a cannulated outer shaft disposed over the inner shaft and the bushing such that the cannulated outer shaft is axially translatable along the central longitudinal axis.

In some examples, the method of the second embodiment may include anchoring the implant in place at the target tissue location prior to withdrawing the implant delivery instrument. Anchoring may be via staples, sutures, or other anchoring methods.

In some examples, the method of the second embodiment may include sliding the bushing toward the proximal end of the inner shaft to the unlocked position occurs after sliding the cannulated outer shaft toward the proximal end of the inner shaft such that prior to sliding the bushing, the clamp and the jaw hold the implant and the implant is exposed from the cannulated outer shaft.

In some examples, the method of the second embodiment may include sliding the cannulated outer shaft toward the proximal end of the inner shaft to cause a plurality of prongs of the clamp to spread apart relative to each other.

In some examples, the method of the second embodiment may include, prior to delivering the implant delivery instrument, adjusting a spacing between a plurality of prongs of the clamp while the clamp is exposed from the cannulated outer shaft.

In some examples, the method of the second embodiment may include sliding the bushing toward the proximal end of the inner shaft to the unlocked position to cause the clamp to move away from the jaw, a position of the jaw relative to the inner shaft remaining unchanged based on the sliding of the bushing.

In some examples, the method of the second embodiment may include sliding the bushing toward the proximal end of the inner shaft to the unlocked position such that a width of the jaw remains unchanged.

BRIEF DESCRIPTION OF THE DRAWINGS

A more complete appreciation for the subject matter of the present disclosure and of the various advantages thereof can be realized by reference to the following detailed description in which reference is made to the accompanying drawings in which.

DETAILED DESCRIPTION

Figure 1:
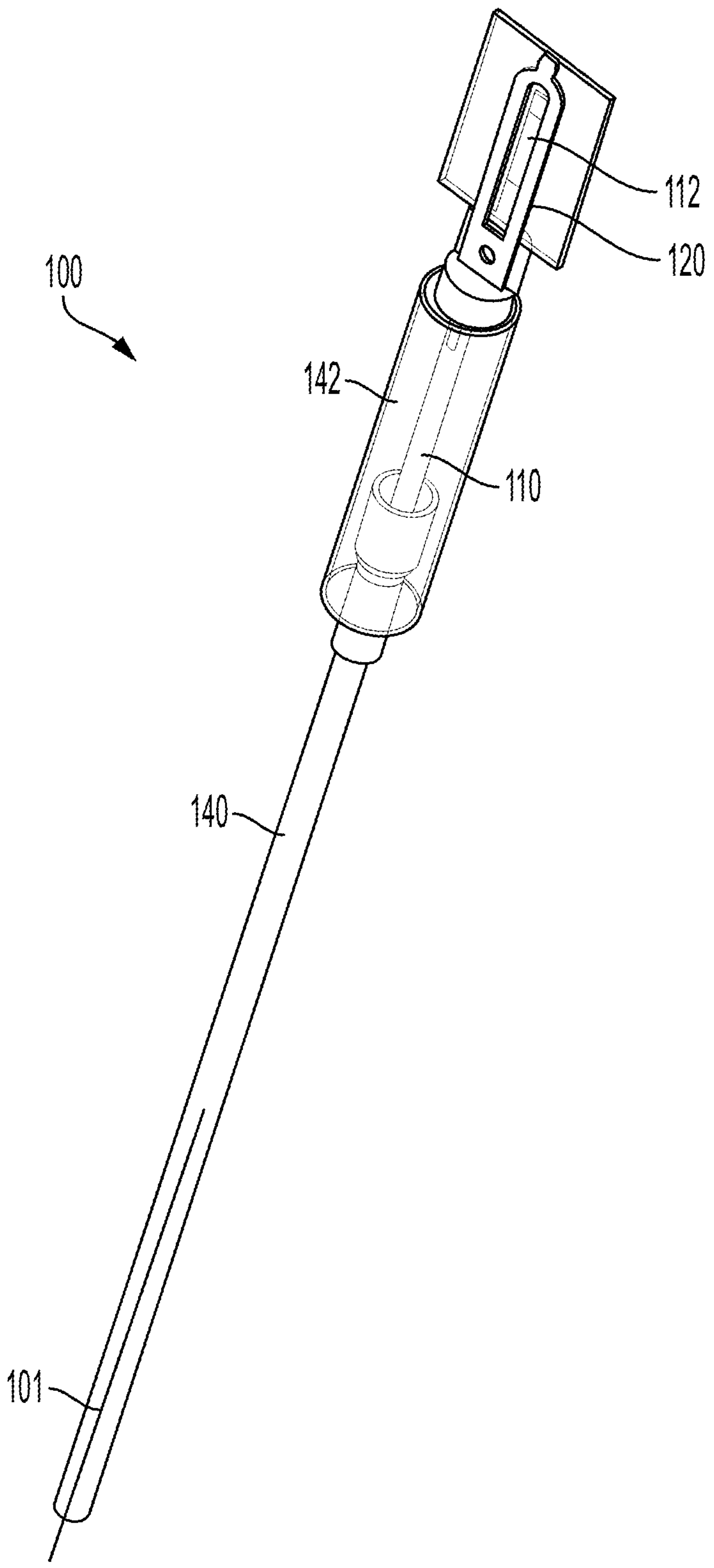
FIG. 1 is a perspective view of a delivery instrument according to one embodiment of the disclosure.

As used herein unless stated otherwise, the term "proximal" means closer to a handle or other gripping portion of an instrument held by a user, and the term "distal" means closer to an opposite end of the instrument remote from the handle. As used herein, the terms "about," "approximately," "generally," and "substantially" are intended to mean that slight deviations from absolute are included within the scope of the term so modified.

In one aspect, the present disclosure relates to a delivery instrument for use in delivering an implant into a patient in a minimally invasive manner. The delivery instrument may be used to repair a rotator cuff, such as the tendons of the rotator cuff. While reference is made throughout the disclosure to repair of the shoulder, and the rotator cuff in particular, it should be appreciated that the delivery instrument may be used for surgical procedures throughout the human body. For example, the delivery instrument may be used for Achilles tendon repair, pectoralis major repair and superior capsule reconstruction.

One embodiment of the delivery instrument is shown in FIGS. 1-5 and indicated by reference numeral 100. Delivery instrument 100 includes a central shaft 110 extending in a proximal-distal direction along a central longitudinal axis 101 to a distal end from which a first gripper 112 and a second gripper 120 extends. A distal end region of the instrument including the grippers may also be referred to as an implant engagement portion. The instrument is further arranged so that an outer shaft 140 with an elongate housing 142 attached thereto is disposed over the central shaft. In this manner, central shaft 110 passes through a lumen of outer shaft 140. The central and outer shafts are operatively connected so that the outer shaft is slidable relative to the central shaft.

Figure 2:
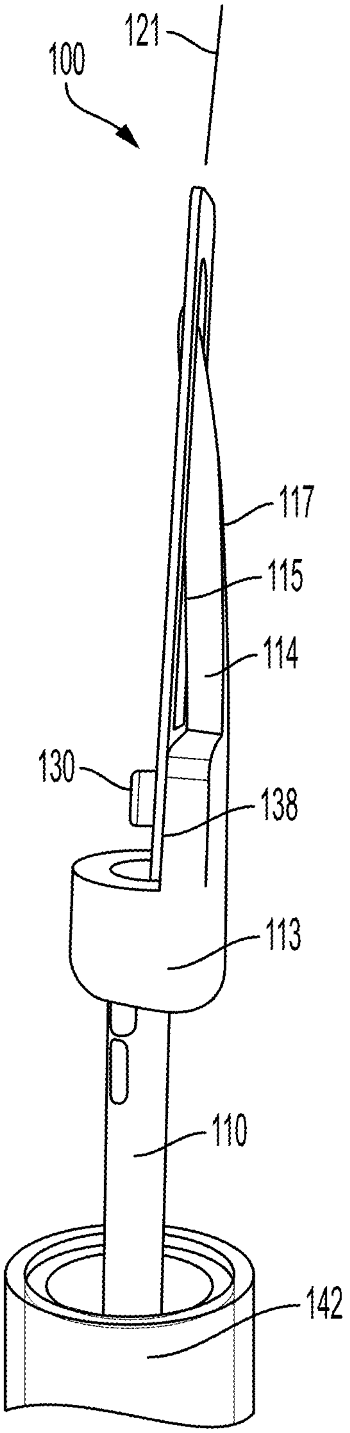
FIGS. 2 and 3 are side and bottom views, respectively, of a distal end portion of the delivery instrument of FIG. 1.
Figure 3:
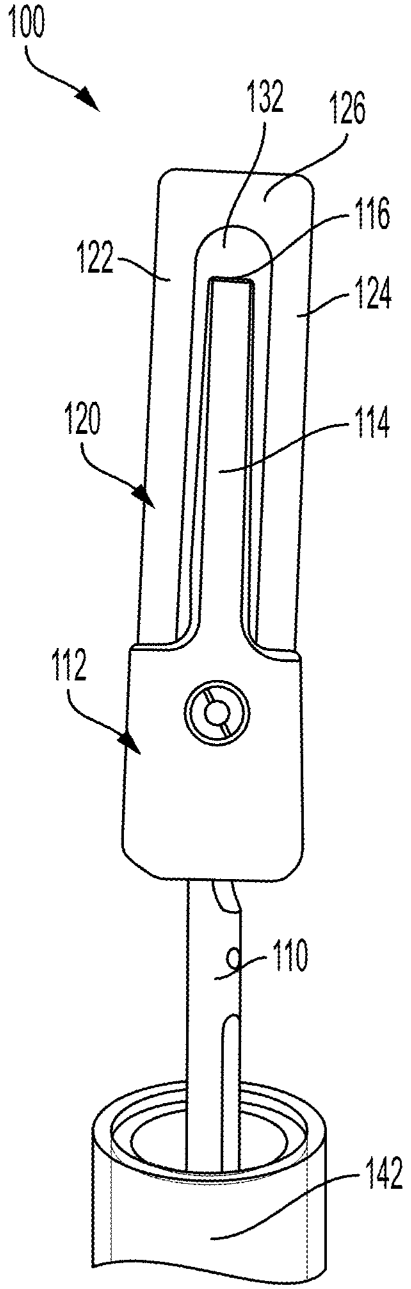

Turning to the gripping features of instrument 100, first gripper 112 is attached to a distal end of central shaft 110, as shown in FIGS. 2 and 3, for example. First gripper 112 includes a base 113 and a jaw 114 extending distally therefrom. As shown in the embodiment as depicted, second gripper 120 is attached to first gripper 112 through a fastener 130, where the fastener passes through a base strip 128 of the second gripper 120 and a surface 138 of base 113. In some examples, other attachment locations and means may be used. Additionally, it should be appreciated that in still further examples, the first and second gripper may be formed through molding techniques that do not require a fastener to connect the first and second gripper together. In some of these examples, the first and second gripper may be formed monolithically. First gripper 112 may have physical properties such that it is more rigid than second gripper 120. To produce first gripper 112 and second gripper 120 having different rigidities, each may be formed using materials having different flexural properties. In examples where first and second grippers 112, 120 are formed monolithically, first gripper 120 may be formed as thicker than second gripper 120 so that the first gripper is more rigid than the second gripper. When formed monolithically, the first and second grippers may be formed through a machining process or a coining process, among other fabrication processes.

Figure 4:
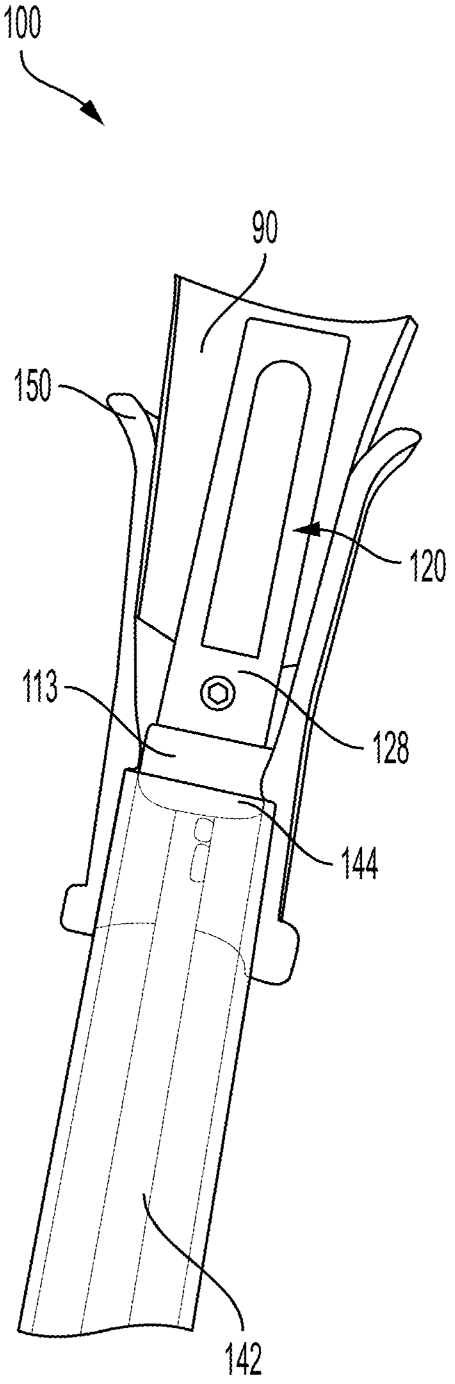
FIG. 4 is a top view of the distal end portion of the delivery instrument of FIG. 1 in a deployed position.

Second gripper 120 includes a series of strips that define a ring-shaped member or a closed loop with an opening therein. As shown in FIG. 4, these include base strip 128, lateral strips 122, 124, and end strip 126. A space between the strips defines opening 132. Opening 132 is sized and positioned so that jaw 114 passes into the opening without contacting lateral strips 122, 124. Second gripper 120 is also biased such that in a neutral state, the second gripper, moving distally from base 113, curves away from a central plane coincident with base strip 128 into a side of the plane including a majority of jaw 114, as best shown in FIG. 2. Further, and with particular attention to FIG. 2, the collective strips, i.e., base strip 128, lateral strips 122, 124 and end strip 126, may generally be coincident with plane 121. The plane 121 may pass through the collective strips where the collective strips define a flat surface or where the collective strips are formed so to have a slight curvature as shown in FIG. 2. In these arrangements, a distal portion of jaw 114 (e.g., tip 116) passes through opening 132 and plane 121 such that when instrument 100 is viewed from the side as in FIG. 2, the distal portion of jaw 114 including tip 116 is on one side of plane 121 and a remainder of jaw 114 is on an opposite side of plane 121. In this manner, and as best shown in FIG. 2, second gripper 120 may be biased so that a tip 116 of jaw 114 passes through the opening 132 when viewed from the side. It should be appreciated that in this arrangement, there is no location where jaw 114 makes contact with any of the strips of second gripper 120. Through this arrangement, and in particular with the second gripper 120 being biased in the manner described, any implant received between first gripper 112 and second gripper 120 may be subject to pressure from the second gripper 120, thereby improving the hold of the instrument on the implant. The second gripper may also be referred to as a closed loop overlay in that when in use, the second gripper presses against an implant.

Figure 5:
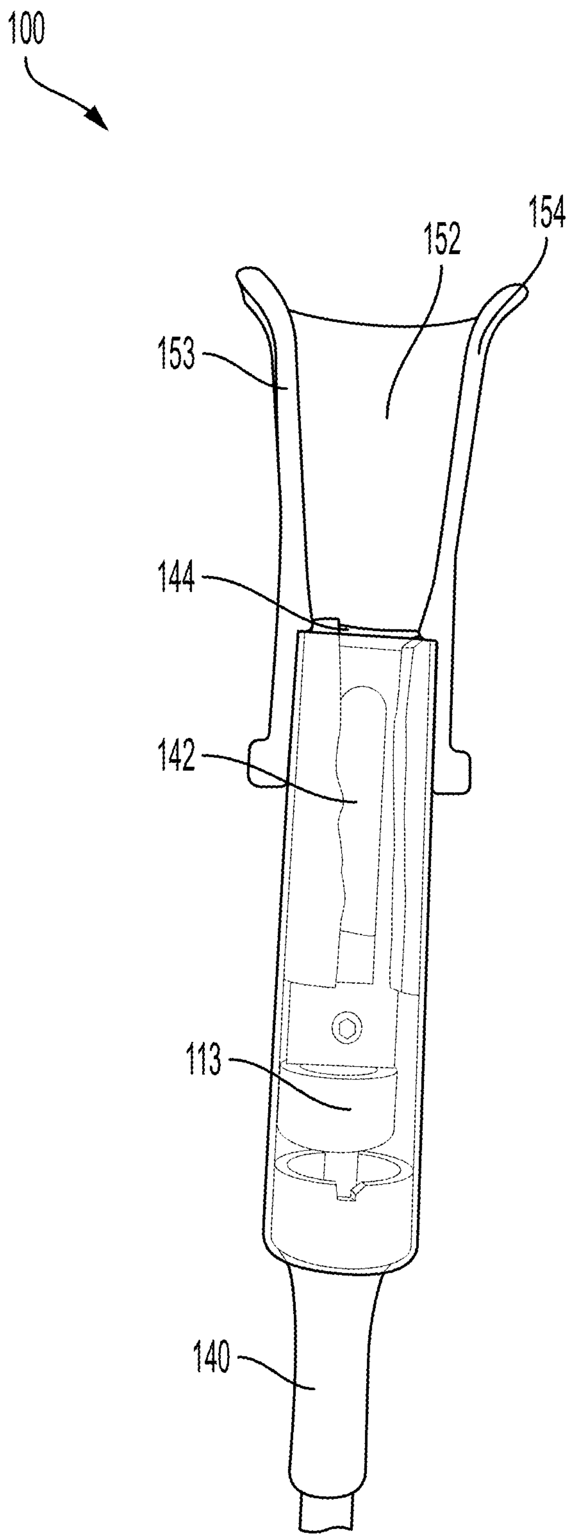
FIG. 5 is a top view of the distal end portion of the delivery instrument of FIG. 1 in an enclosed position.

Elongate housing 142 is hollow and as described above, is arranged so that it may be translated over the central shaft 110 between a retracted position and an extended position. In terms of an overall description of a position of the delivery instrument, the retracted position of the elongate housing deploys the gripping components (e.g., first gripper 112 and second gripper 120) and in such position the instrument is referred to as being in a deployed position. When the elongate housing is in the extended position, the elongate housing encloses the gripping components and the instrument is referred to as being in an enclosed position. For delivery instrument 100, elongate housing 142 has an inner diameter large enough such that second gripper 120 fits entirely therein as elongate housing 142 passes over it, as shown in FIG. 5. In this way, the elongate housing need not contact the second gripper as it is moved between the retracted and the extended positions, and for this reason the second gripper does not need to flex during operation of the elongate housing 142. In some examples, elongate housing 142 may be made of a clear material. With the elongate housing formed of a clear material, a user may visualize the implant when enclosed within the elongate housing, as is shown in FIG. 5, for example. In alternative examples, the elongate housing may have an opaque exterior and/or be made of an opaque material, such as a metal. In such examples, the elongate housing may include slots, windows or both to allow for visualization of contents within the elongate housing, such as an implant when enclosed therein.

While methods of using delivery instrument 100 are described in greater detail elsewhere in the application, a further component that may be included with the instrument is a funnel 150, as shown in FIGS. 4-5. The funnel may have a semi-cylindrical shape and be sized to snap onto an outside of elongate housing 142. It should be appreciated that funnel 150 may be also used with any other contemplated embodiment of the delivery instrument, such as delivery instrument 200, 300, 400, 400, 500, 600, 700, 800, 900 and 1000.

At its most fundamental, delivery instrument 100 is operative provided that central shaft 110 may be held still while outer shaft 140 is either advanced or retracted relative to central shaft 110. In some examples, a proximal end of instrument 100 may include a physical structure that renders axial translation of outer shaft 140 relative to central shaft 110 more amenable for manipulation by a user. Such physical structure may be a simple extension on the central shaft 110 that allows the central shaft to be stabilized, i.e., held in place, while the outer shaft 140 is translated. Such extension may include a handle or another grip, for example. In one example, instrument 100 may include a handle structure similar to that shown in FIG. 21, another embodiment of the present disclosure. In this manner, instrument 100 may include a handle such as handle 775 along with a sliding block disposed in the handle, the sliding block being in operative communication with outer shaft 140 to control a position of the outer shaft 140 relative to the handle and the central shaft 110. Other exemplary actuation configurations include a plunger-type actuator and a trigger-type actuator, where the actuator controls axial displacement of outer shaft 140 relative to central shaft 110.

Various combinations of materials may be used to fabricate the components of delivery instrument 100. In some examples, first gripper 112 may be made of Polyether ether ketone (PEEK) and second gripper 120 may be made of nitinol. In some examples, the second gripper may be made of a stainless steel. One example of stainless steel that may be used is a premium melted, martensitic, age-hardenable stainless steel alloy sold under the trademark CUSTOM 465® by Carpenter Technology Corporation of Philadelphia, PA. In other examples, the first and second grippers may be formed of a single material. Differences between materials used may be accounted for through adjustment of a thickness of the component at issue. For example, if a single material is used and it is desired to make a first part of the instrument stiffer than a second part, the first part may be formed with a greater thickness than the second part. Stated differently, adjustment of a component thickness may be used to modify an expected flexural characteristic of the component. As to elongate housing 142 and funnel 150, in some examples, the elongate housing and funnel may be made of polymeric materials. In other examples, the elongate housing may be metallic. While reference is made to delivery instrument 100 for the above description of materials, it should be appreciated that the same materials may be used for other embodiments contemplated by the present disclosure, including, for example, delivery instrument 200, 300, 400, 400, 500, 600, 700, 800, 900 and 1000.

Figure 6:
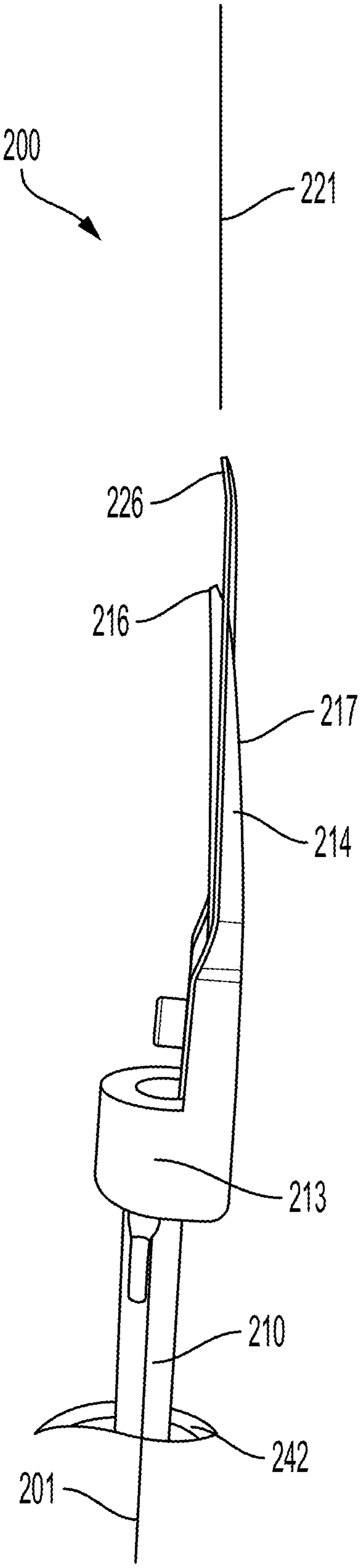
FIGS. 6 and 7 are side and bottom views, respectively, of a distal end portion of a delivery instrument according to one embodiment of the disclosure.
Figure 7:
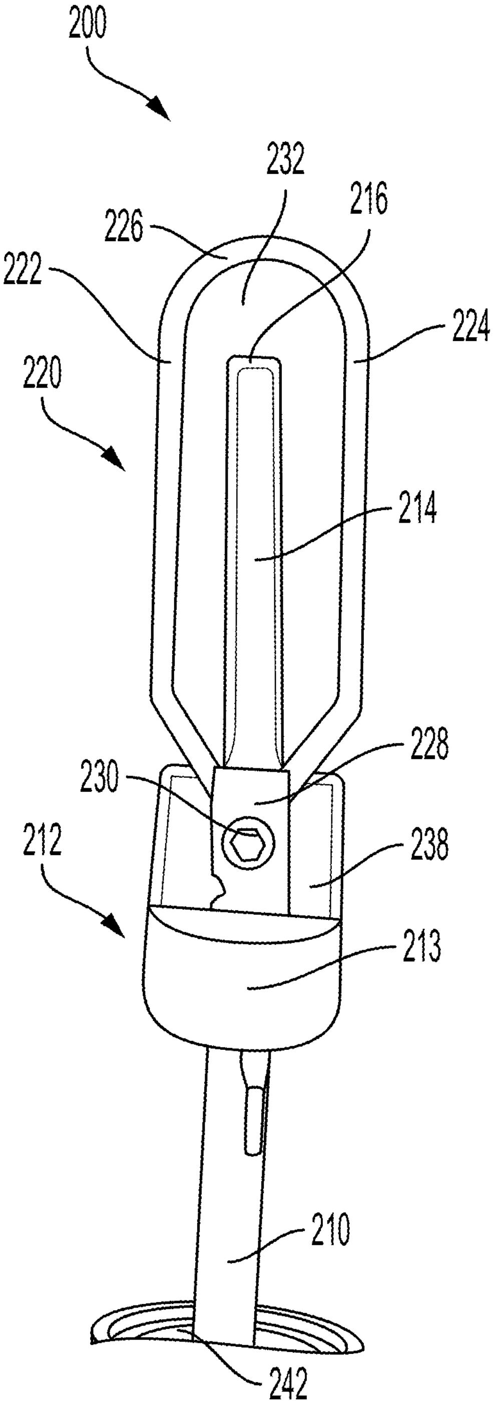

In another embodiment, delivery instrument 200 is shown in FIGS. 6-7. Reference numerals in the 200-series of numerals for delivery instrument 200 refer to like elements in the 100-series of numerals for delivery instrument 100 unless otherwise indicated. As depicted, delivery instrument 200 includes a central shaft 210 with a first gripper 212 and a second gripper 220 attached to a distal end region of the central shaft. Second gripper 220 is attached to first gripper 212 via a fastener 230. The first gripper 212 includes a jaw 214 that extends to a tip 216. The second gripper 220 includes a base strip 228 that is positioned on a surface 238 of the first gripper. First and second lateral strips 222, 224 extend distally from base strip 228. The lateral strips as shown initially extend diagonally from the base strip and then run in parallel to respective distal ends. In other examples, the diagonal angulation may be varied. Distal ends of the respective lateral strips may be connected to each other through end strip 226. In some examples, end strip 226 may be curved as shown in FIG. 7. In other examples, end strip 226 may be orthogonal to a longitudinal axis along a length of the instrument or may have other desired geometry. An overall shape of the collective strips, i.e., base strip 228, lateral strips 222, 224 and end strip 226, may be an oval or similar to an oval, as shown in FIG. 7. As also shown in FIG. 7, strips 222, 224, 226, 228 collectively define an opening 232 therebetween. Additionally, the collective strips may generally be coincident with plane 221. The collective strips may be coincident with the plane 221 where the collective strips define a flat surface or where the collective strips are formed so to have a slight curvature as shown in FIG. 6. In these arrangements, a distal portion of jaw 214 (e.g., tip 216) passes through opening 232 and plane 221 such that when instrument 200 is viewed from the side as in FIG. 6, the distal portion of the jaw 214 including tip 216 is on one side of plane 221 and a remainder of the jaw 214 is on an opposite side of plane 221. As with instrument 100, second gripper 220 may be biased. For delivery instrument 200, second gripper 220, moving distally from base 213, curves away from a central plane through base strip 228 into a side of the plane including a majority of a back side 217 of jaw 214. Such shape ensures that an implant received between the grippers is subject to pressure by the second gripper and is held in place. As shown in FIG. 6, a surface of second gripper 220 facing away from back side 217 of the jaw is concave, though in variations, such surface may be convex as in delivery instrument 100. It should be appreciated that such concave and convex surface alternatives may also be interchangeable in other embodiments of the disclosure, including delivery instrument 100, for example.

Each lateral strip 222, 224 is shaped so that a maximum width dimension between and including the lateral strips, the width being orthogonal to a central longitudinal axis 201 of central shaft 210, is larger than a maximum cross-sectional dimension of first gripper 212 measured orthogonal to the central longitudinal axis, which may be a cross-sectional dimension of base 213. Further, the maximum width spanning first and second lateral strips 222, 224 is larger than an inner diameter of elongate housing 242. However, second gripper 220 is formed of a flexible material, such as nitinol, and thus during use of instrument 200 when elongate housing 242 is advanced distally over the first and second gripper to the extended position, first and lateral strips 222, 224 deform to fit within the lumen of elongate housing 242. This configuration allows for a larger surface area for contacting an implant received by the grippers of the instrument, while also allowing for delivery of the implant within a relatively narrow cannula via elongate housing 242.

Figure 8:
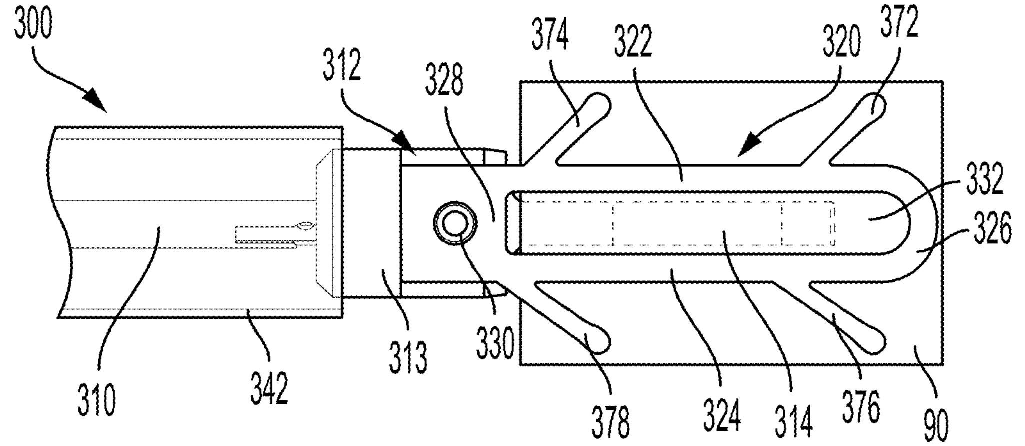
FIG. 8 is a top view of a distal end portion of a delivery instrument in a deployed position according to one embodiment of the disclosure.
Figure 9:
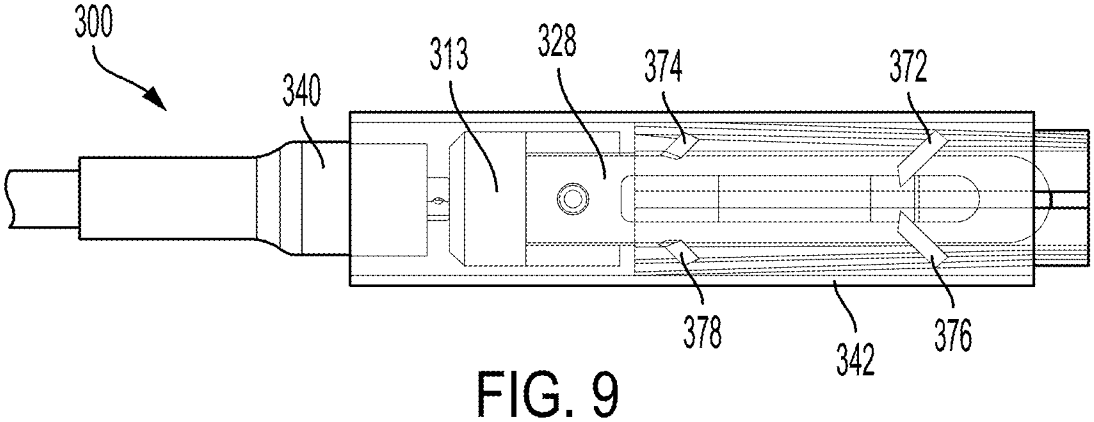
FIGS. 9 and 10 are top and side views, respectively, of the distal end portion of the delivery instrument of FIG. 8 in an enclosed position.
Figure 10:
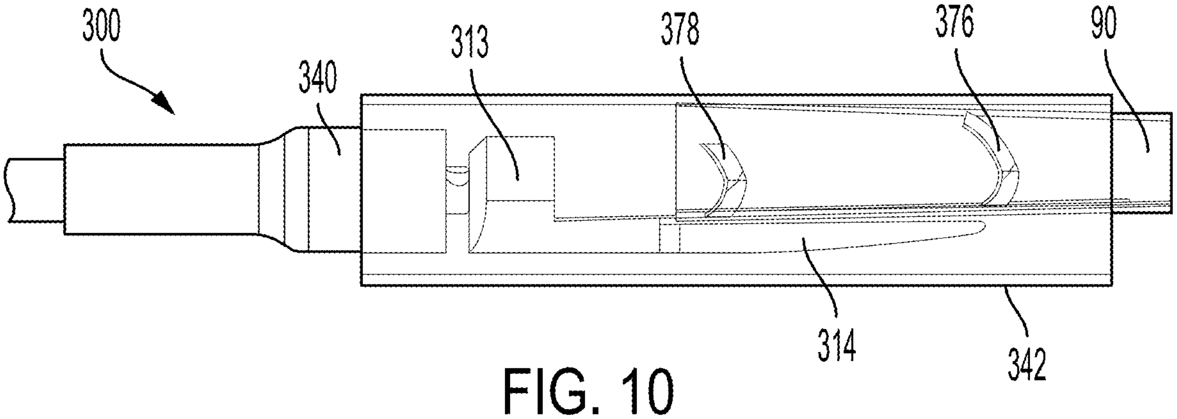

In another embodiment, delivery instrument 300 is shown in FIGS. 8-10. Reference numerals in the 300-series of numerals for delivery instrument 300 refer to like elements in the 100-series of numerals for delivery instrument 100 unless otherwise indicated. Delivery instrument 300 includes a central shaft 310 with an implant engagement portion attached thereto. The implant engagement portion includes a first gripper 312 and a second gripper 320 attached to the first gripper. First gripper 312 includes a jaw 314 extending distally to a tip 316. Second gripper 320 includes a base strip 328, distally extending lateral strips 322, 324, each extending from base strip 328, and end strip 326 joining the lateral strips at their respective distal ends. These strips collectively define opening 332 therebetween, as best shown in FIG. 8. A maximum width dimension across lateral strips 322, 324, the width dimension being orthogonal to a central longitudinal axis of the central shaft, is less than an inner diameter of elongate housing 342 such that there is no interference between inner surfaces of the elongate housing and the lateral strips when the elongate housing is advanced over the second gripper.

Second gripper 320 also includes one or more branches that each extend at least partially in a lateral direction from one or both of lateral strips 322, 324. It is contemplated that instrument 300 may include any number of branches. As shown in FIGS. 8-10, delivery instrument 300 includes four branches, two branches 372, 374 extending from lateral strip 322, and two branches 376, 378 extending from lateral strip 324. Each branch may have a single width extending to a free end. In some examples, the branches may have a bulging surface area at their free ends. Each branch extends laterally away from one of the lateral strips 322, 324 and distally. For example, each branch may extend from a lateral strip at a 30-60 degree angle, though designs are not limited to such range. Each branch 372, 374, 376, 378 is spaced apart from a distal end of the second gripper at the end strip 326 such that at least a portion of one of lateral strips 322, 324 separates the branches from end strip 326. Further, when viewed from above as shown in FIG. 8, branches on opposite lateral sides are axially offset from each other such that the second gripper is not symmetrical. For example, branch 372 is a different distance from the distal end of the second gripper than branch 376. In some examples, one or more branches may be biased away from a plane through the lateral strips on a side of the plane including a base of the jaw, i.e., in a direction into the page in FIG. 8. In this manner, when an implant such as implant 90 is received between the first and second gripper, the branches may press against the implant surface and may also promote flattening of the implant. Such bias in the branches may be achieved through heat treatment, molding, plastic deformation and/or any other treatment suitable for producing a biased structure. Second gripper 320 may be partially or entirely formed of flexible materials, such as nitinol.

FIG. 8 illustrates delivery instrument 300 in a deployed position with the grippers exposed, while FIGS. 9-10 illustrate delivery instrument 300 in an enclosed position with elongate housing 342 enclosing at least part of the first and second grippers and any implant 90 held by such grippers. When elongate housing 342 is advanced over the grippers, the branches 372, 374, 376, 378, which span a lateral dimension greater than an inner diameter of the elongate housing, may flex and deform as shown in FIGS. 9-10 to fit within the lumen of the elongate housing. Lateral strips 322, 324 of second gripper 320 may preserve their original shapes when the instrument moves from the deployed position to the enclosed position when a maximum width dimension, i.e., a lateral dimension across the lateral strips, is less than the inner diameter of the elongate housing.

Figure 11:
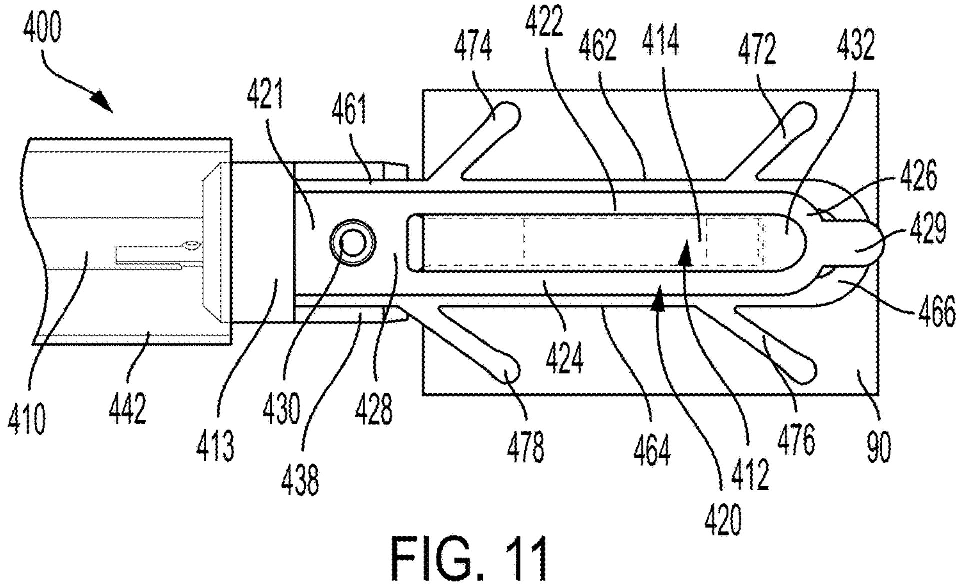
FIG. 11 is a top view of a distal end portion of a delivery instrument in a deployed position according to one embodiment of the disclosure.
Figure 12:
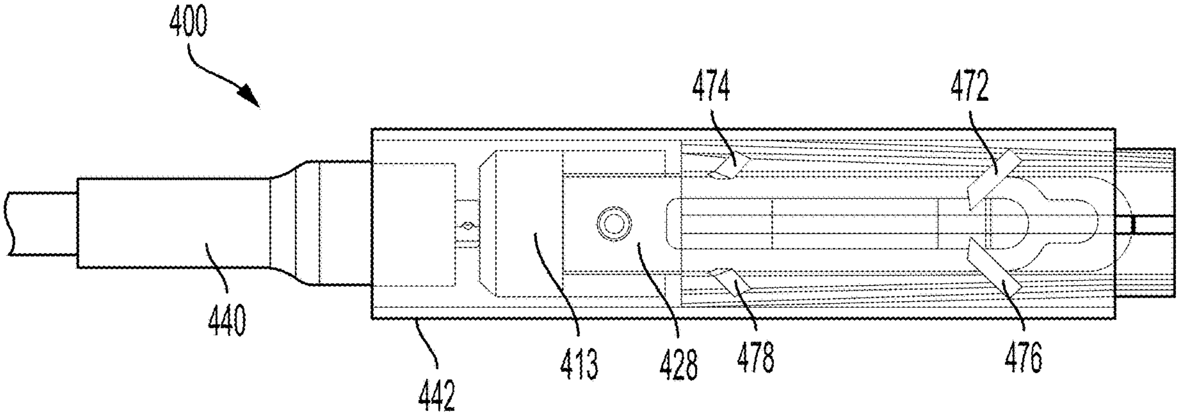
FIGS. 12 and 13 are top and side views, respectively, of the distal end portion of the delivery instrument of FIG. 11 in an enclosed position.
Figure 13:
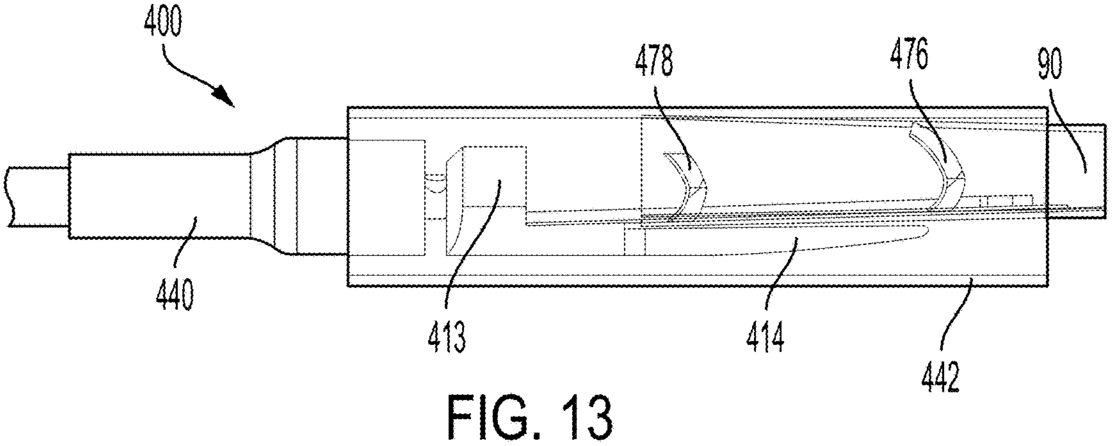

In another embodiment, delivery instrument 400 is shown in FIGS. 11-13. Reference numerals in the 400-series of numerals for delivery instrument 400 refer to like elements in the 100-series of numerals for delivery instrument 100 unless otherwise indicated. Delivery instrument 400, as with certain other embodiments described in the present disclosure, includes a first gripper 412 and a second gripper 420. Second gripper 420 includes a rigid body 421 and a flexible body 461. As depicted in FIGS. 11-13, flexible body 461 is placed directly onto surface 438 of base 413 of the first gripper, while rigid body 421 is positioned directly onto flexible body 461. Rigid body 421 and flexible body 461 of the second gripper may be secured to first gripper 412 via a fastener 430. Both rigid body 421 and flexible body 461 are elongate and extend together along a central longitudinal axis of the instrument, along with jaw 414 of the first gripper, as shown in FIG. 11, for example. In this arrangement, flexible body 461 is disposed in between rigid body 421 and jaw 414.

Rigid body 421 includes base strip 428 and lateral strips 422, 424 extending distally therefrom. Distal ends of the respective lateral strips are joined at an end strip 426, which may be curved as shown in FIGS. 11 and 12 or may have another shape. A space between the strips defines an opening 432. Additionally, a tab 429 may extend distally from end strip 426, as shown. Rigid body 421 may have a maximum width dimension, i.e., a lateral dimension across the lateral strips that is less than an inner diameter of elongate housing 442 such that when elongate housing is passed distally over the grippers, rigid body 421 fits within the lumen of the elongate housing without pressing against internal surfaces of the elongate housing. Rigid body 421 may be less flexible, i.e. more rigid, than flexible body 461. Such difference in rigidity may be provided by forming rigid body 421 with different materials than flexible body 461, or, if the same materials are used, rigid body 421 may be formed with a greater thickness than flexible body 461 to provide a desired difference in rigidity between the components. In some examples where the same materials are used, the rigid and flexible bodies 421, 461 may be formed monolithically from a single piece of material. In such cases, the single piece may be machined to provide a rigid body with a first thickness and a flexible body with a second thickness less than the first thickness. Other techniques for forming the bodies may also be used, such as coining. In variations of delivery instrument 400, the rigid body and the flexible body may have the same degree of rigidity, and of course, in such cases would not be characterized such that one body is more rigid or flexible relative to the other.

Flexible body 461 includes a base strip (not shown) and lateral strips 462, 464 extending distally from the base strip. Distal ends of the respective lateral strips are joined at an end strip 466. An opening defined by the strips may be similar to or larger than opening 432. An outer profile or perimeter of strips 462, 464, 466 may be slightly larger than an outer profile of strips 422, 424, 426, as shown in FIG. 11. In this manner, tab 429 may be positioned directly over end strip 466. In some examples, flexible body 461 and rigid body 421 may be interlocked. Such interlocking may be through a weld, for example. Further, flexible body 461 may also include any number of branches. As shown in FIGS. 11-13, instrument 400 includes four branches, two branches 472, 474 extending from lateral strip 422, and two branches 476, 478 extending from lateral strip 424. Each branch may have a single width extending to a free end. In some examples, the branches may have a bulging surface area at their free ends. Each branch extends laterally away from one of the lateral strips 422, 424 and distally. For example, each branch may extend from a lateral strip at a 30-60 degree angle, though designs are not limited to such range. Each branch 472, 474, 476, 478 is spaced apart from a distal end of the second gripper at the end strip 466 such that at least a portion of one of lateral strips 422, 424 separates the branches from end strip 426. Further, when viewed from above as shown in FIG. 11, branches on opposite lateral sides are axially offset from each other such that the second gripper is not symmetrical. For example, branch 472 is a different distance from the distal end of the second gripper than branch 476. In some examples, one or more branches may be biased away from a plane through the lateral strips on a side of the plane including a base of jaw 414, i.e., in a direction into the page in FIG. 11. In this manner, when an implant such as implant 90 is received between the first and second gripper, the branches may press against the implant surface. Bias in the branches of delivery instrument 400 may be obtained through the approaches described for delivery instrument 300, for example.

Flexible body 461 of the second gripper may be partially or entirely formed of flexible materials, such as nitinol. In some examples, flexible body 461 may be biased such that in a neutral unloaded condition, flexible body 461 bends in an arcuate manner so that it becomes closer to and/or presses against rigid body 421 in a central region of the rigid body approximately mid-way between base strip 428 and end strip 426. When flexible body 461 is biased in such manner, a central part of the flexible body along its length may maintain at least some contact with rigid body 421. Additionally, such bias may also further promote additional surface area pressure against any implant received between first and second grippers 412, 420 due to distal portion of flexible body 461 curving away from rigid body 421 toward the implant. In terms of manipulation of the flexible body to receive an implant, in the described arrangement, flexible body 461 may be lifted to provide temporary space for insertion of an implant between the grippers, with the flexible body 461 reverting back to its biased state when released. In other examples, flexible body 461 may have minimal bias in its neutral state. In such arrangements, an orientation of the second gripper may be directed so that the flexible and rigid bodies are more closely aligned with the jaw in terms of their relative elevational position when viewed from a side of the instrument. In still further examples, rigid body 421 may also be biased in a neutral unloaded condition so that when an implant is received between the first and second grippers, pressure is applied by the second gripper onto the implant.

FIG. 11 illustrates delivery instrument 400 in a deployed position with the grippers exposed while FIGS. 12-13 illustrate delivery instrument 400 in an enclosed position with elongate housing 442 enclosing at least part of the first and second grippers and any implant 90 held by such grippers. When elongate housing 442 is advanced over the grippers, the branches 472, 474, 476, 478, which span a lateral dimension greater than an inner diameter of the elongate housing, may flex as shown in FIGS. 12-13 to fit within the lumen of the elongate housing. Rigid body 421 of second gripper 320 may preserve its original shape when the instrument is moved from the deployed position to the enclosed position because a maximum width dimension, i.e., lateral dimension across the lateral strips is less than the inner diameter of the elongate housing. In some examples, strips 462, 464 may also preserve their original shape when the instrument is moved from the deployed position to the enclosed position, for the same reasons. In still further examples, a maximum width dimension across the lateral strips 462, 464 may be larger than the inner diameter of elongate housing 442, and in such cases, the lateral strips may flex and deform to fit into elongate housing 442 when the instrument is moved to the enclosed position.

As explained above, in some variations of delivery instrument 400, rigid body 421 and flexible body 461 may be formed monolithically. With the use of a single material for both parts of the second gripper, greater flexibility in the flexible body may be obtained by making the flexible body thinner than the rigid body.

Figure 14:
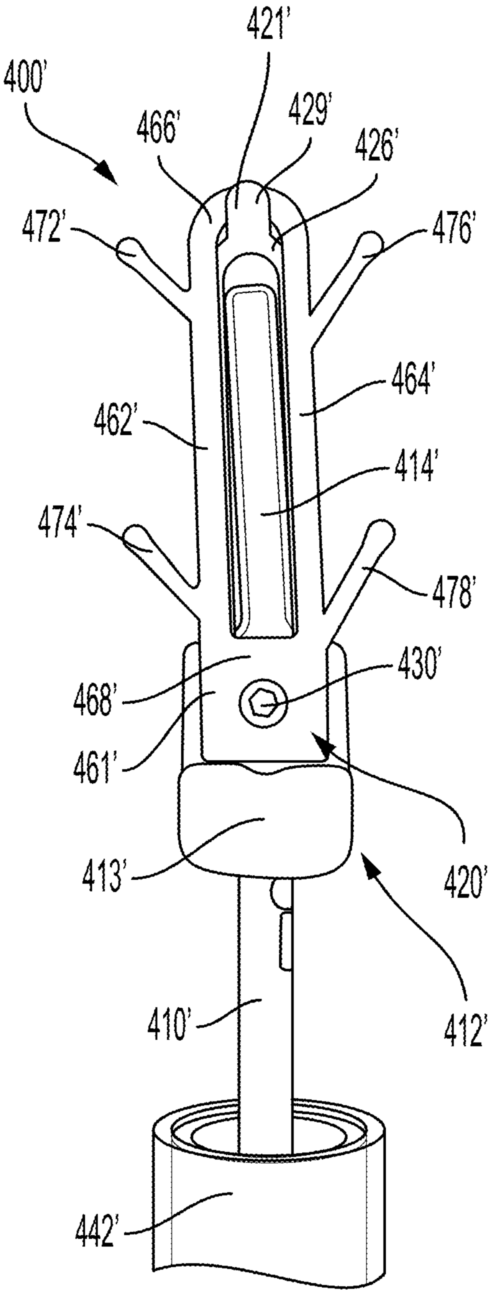
FIGS. 14 and 15 are top and side views, respectively, of a distal end portion of a delivery instrument according to one embodiment of the disclosure.
Figure 15:
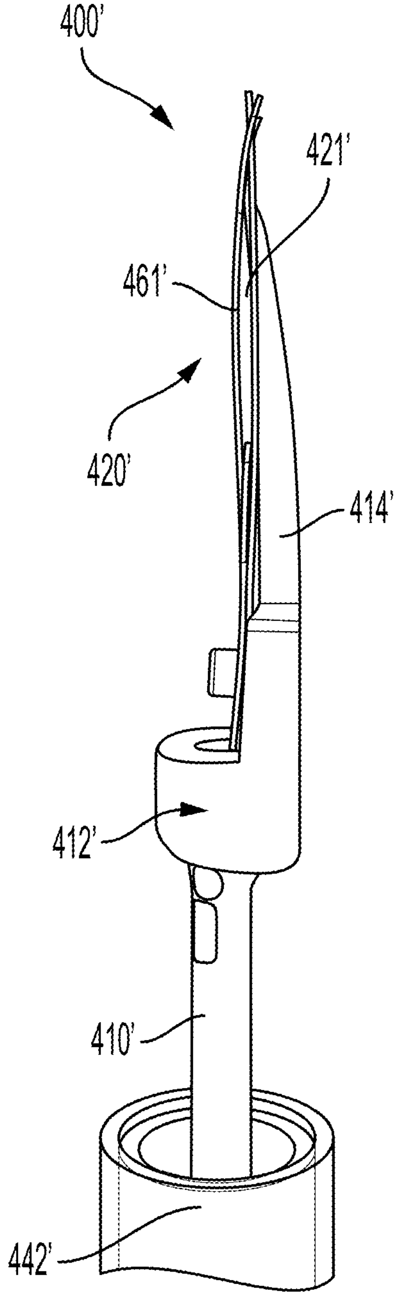

In another embodiment, delivery instrument 400' is shown in FIGS. 14-15. Reference numerals in the 400 prime (400')-series of numerals for delivery instrument 400 refer to like elements in the 400-series of numerals for delivery instrument 400 unless otherwise indicated. Delivery instrument 400', as with delivery instrument 400, includes first gripper 412' and second gripper 420', where the second gripper includes rigid body 421' and flexible body 461'. However, delivery instrument 400' is distinguishable from instrument 400 in that rigid body 421' is disposed directly on base 413' of first gripper 412' with flexible body 461' placed over rigid body 421' so that the rigid body is in between the first gripper and the flexible body as shown in FIG. 14. Further, in this arrangement, flexible body 461', having greater flexibility than the rigid body, may be brought over or otherwise be positioned over a tab 429" of rigid body such that flexible body buckles outward away from jaw 414, as shown in FIG. 15. That is, as shown in FIG. 15, the tab 429' passes through the opening defined by the flexible body 461' from one side of the plane defined by the flexible body 461' (where the rigid body 421' is positioned) to the opposite side of the plane. In this manner, end strip 466' of the flexible body is prevented from becoming further displaced relative to jaw 414' by pressing against tab 429'. Flexible body 461' may be formed with a bias such that it has an arcuate profile in a neutral state or, in some examples, may have a flat or nearly flat profile in a neutral state, with the buckled shape occurring upon securement under the tab.

The first and second gripper of delivery instrument 400' are arranged such that an implant (not shown) may be positioned into a space between the first and second gripper through drawing a distal end of the flexible body away from the jaw to create the space. Such action may also cause rigid body to move to a small extent depending on the degree of force applied. Variations or similarities in the material properties of the rigid body 421' and flexible body 461' may be the same as those described for delivery instrument 400. Similarly, the rigid body 421' and flexible body 461' may be separate bodies or formed as a monolithic structure as described for delivery instrument 400.

Figure 16:
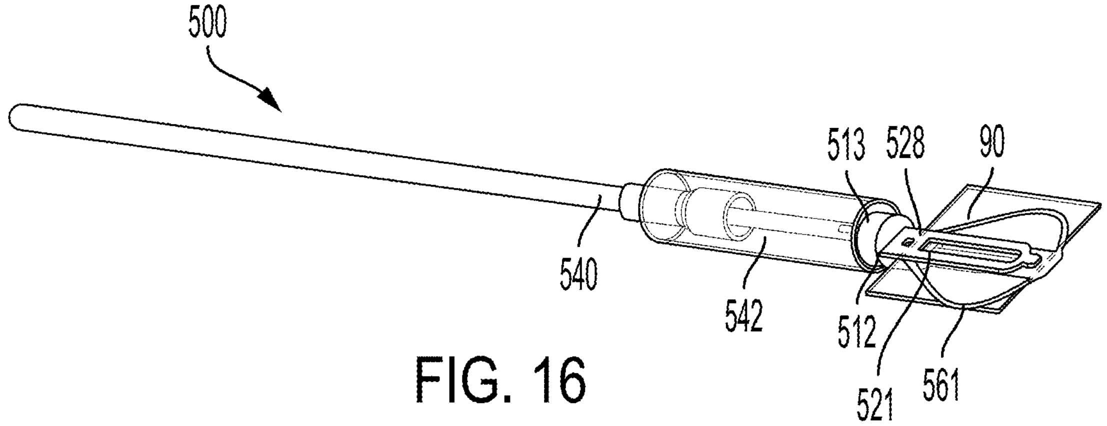
FIG. 16 is a perspective view of a delivery instrument according to one embodiment of the disclosure.
Figure 17:
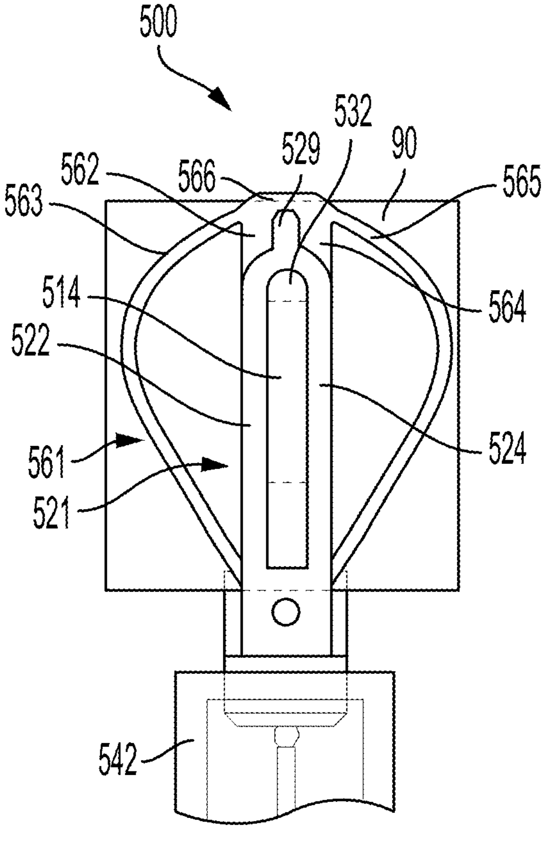
FIG. 17 is a top view of a distal end portion of the delivery instrument of FIG. 16 in a deployed position.
Figure 18:
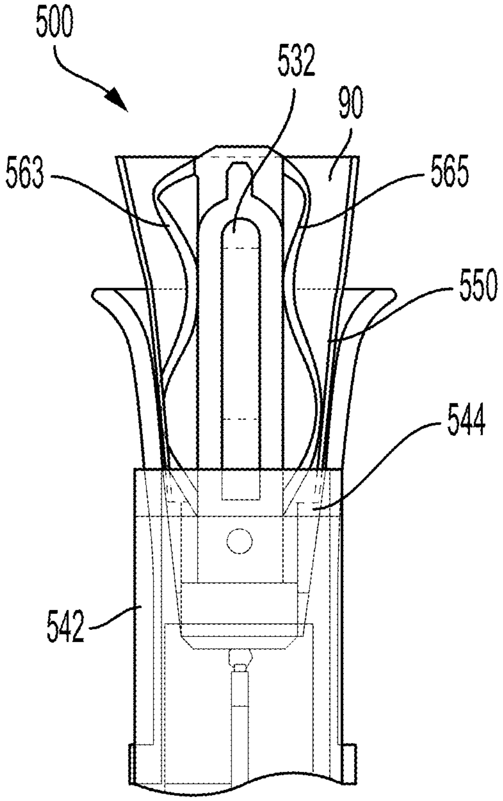
FIG. 18 is a top view of a distal end portion of the delivery instrument of FIG. 16 in aa partially enclosed position.

In another embodiment, delivery instrument 500 is shown in FIGS. 16-18. Reference numerals in the 500-series of numerals for delivery instrument 500 refer to like elements in the 400-series of numerals for delivery instrument 400 unless otherwise indicated. Delivery instrument 500 includes an implant engagement portion extending from a central shaft, the implant engagement portion including a rigid body 521 and a flexible body 561. Flexible body 561 is positioned directly onto first gripper 512 while rigid body 521 is positioned directly onto flexible body 561, as shown in FIGS. 17-18. Rigid body may include a tab 529 extending over an end strip 566 of flexible body 561. Flexible body 561 includes lateral strips 562, 564 extending longitudinally toward a distal end of the implant engagement portion, connected to each other via end strip 566. Extending laterally outward on both sides of end strip 566 are wing strips 563, 565, respectively, such wing strips having a curved shape in a neutral state as shown in FIG. 17, with each extending away from an adjacent lateral strip moving proximally from end strip 566 and then after reaching an apex, extending back toward base strip 528. As depicted, the respective wing strips 563, 565 may be symmetrical. In variations, the wing strips may be offset in their axial position or have differing neutral shapes.

In delivery instrument 500, part or all of flexible body 561 may be more flexible than rigid body 521. In examples such as that shown in FIGS. 16-18, at least wing strips 563, 565 have a flexible property such that the application of low levels of force, e.g., through the attachment of funnel 550 to an end of elongate housing 542 as shown in FIG. 18 or through the advancement of elongate housing over the implant engagement portion, causes wing strips 563, 565 to buckle and/or otherwise deform to fit within a remaining constrained physical space. Thus, while a lateral span of wing strip 563 to wing strip 565 is greater than an inner diameter of elongate housing 542, such wing strips 563, 565 may be received within elongate housing 542 when forces are applied to constrain the wing strips. Additionally, one or both of wing strips 563, 565 may be biased in a direction away from a plane through rigid body 521 on a side of the plane including at least a base of the jaw such that when an implant is received between the first and second gripper, the wing strips will press against the implant surface both to keep ahold of the implant, e.g., graft, as well as to keep the implant flattened. As shown in FIGS. 16-18, flexible body 561 is a monolithic structure and rigid body 521 is a separate monolithic structure. In some variations, the wing strips may be formed separately from the lateral strips, end strip, and/or base strip of the flexible body and may be fixed thereto. Fixation may be accomplished through welding or other known techniques. Each of FIGS. 16-18 illustrate implant 90 when held by the delivery instrument 500. In practice, implant 90 is between jaw 514 and flexible body 561, as shown in FIGS. 16-18. Additionally, as shown in FIG. 18, implant 90 is folded and or crumpled into funnel 550 when funnel 550 is attached to elongate housing 542 and elongate housing 542 is partially advanced over rigid and flexible bodies 521, 561. A process of such folding would commence at a proximal end of the implant. In FIG. 18, delivery instrument 500 is in a partially enclosed position.

Variations or similarities in the material properties of the rigid body 521 and flexible body 561 may be the same as those described for delivery instrument 400. Similarly, the rigid body 521 and flexible body 561 may be separate bodies or formed as a monolithic structure as described for delivery instrument 400. Thus, in some variations, flexible body and rigid body may be formed from a single material as a single monolithic structure. One example of this is shown in FIGS. 19-20 and described in greater detail below.

Figure 19:
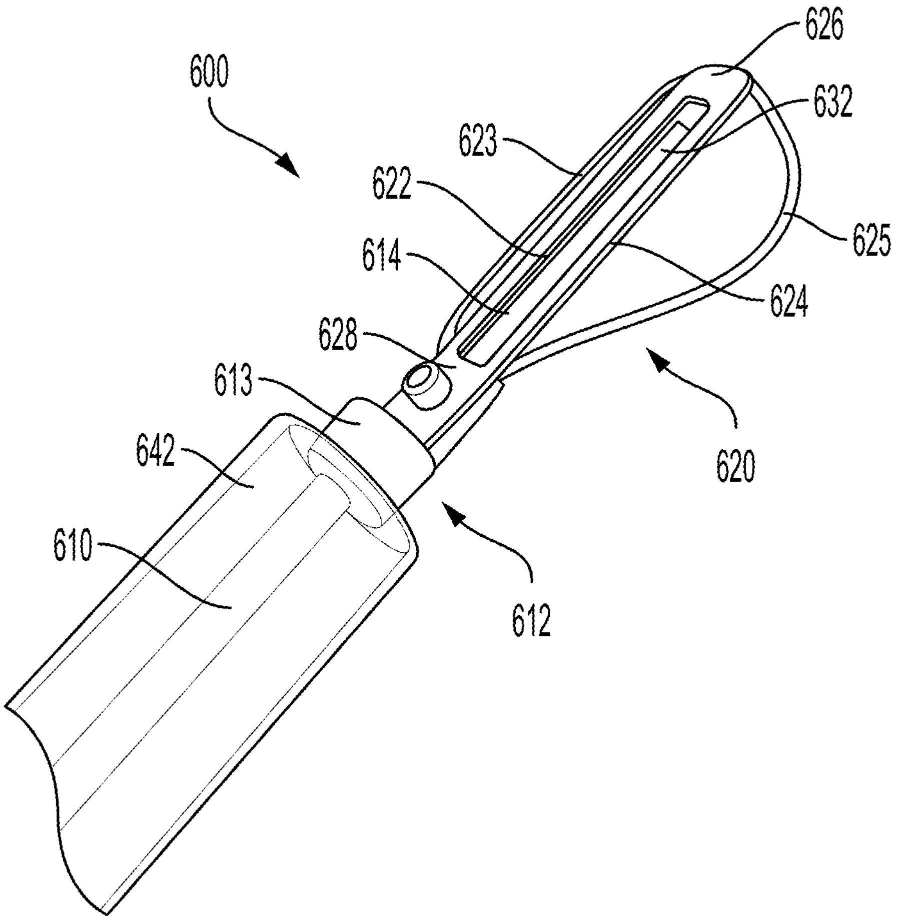
FIGS. 19 and 20 are perspective and side views, respectively, of a delivery instrument according to one embodiment of the disclosure.
Figure 20:
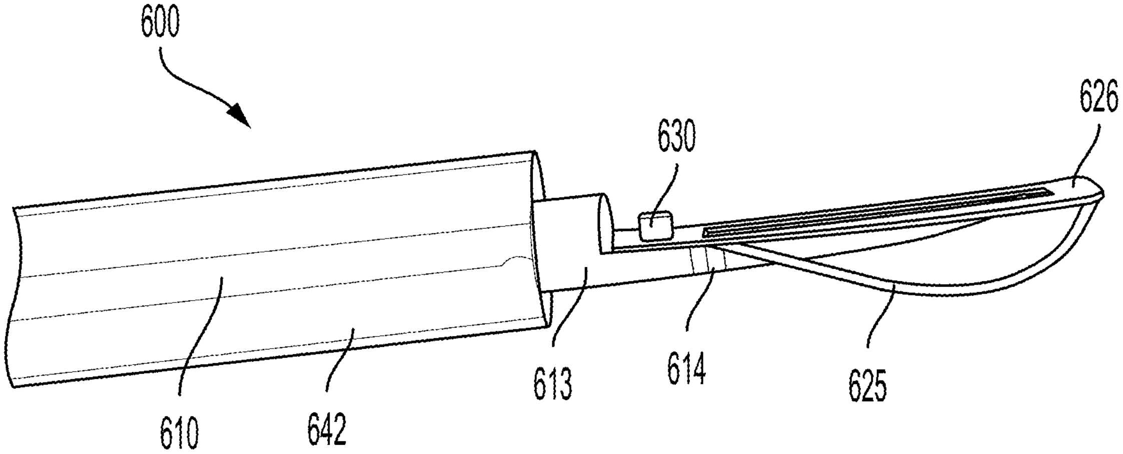

In another embodiment, delivery instrument 600 is shown in FIGS. 19-20. Reference numerals in the 600-series of numerals for delivery instrument 600 refer to like elements in the 400-series of numerals for delivery instrument 400 unless otherwise indicated. Delivery instrument 600 includes an implant engagement portion with a first gripper 612 and a second gripper 620. The first gripper includes jaw 614 and the second gripper includes a base strip 628 secured to a surface of the first gripper. In one example, this may be through a fastener 630. Second gripper 620 further includes lateral strips 622, 624 extending distally from base strip 628 toward a distal end of the implant engagement portion, such lateral strips being joined by an end strip 626, as shown in FIG. 19. Second gripper also includes wing strips 623, 625.

As depicted, each wing strip extends along a length of the second gripper by extending laterally outward from base strip and also in a distal direction to an apex from which the wing strip curves back to end strip 626. The wing strips may be formed monolithically with a remainder of second gripper or may be attached thereto via a weld, for example. Additionally, wing strips 623, 625 are biased in a direction away from a plane through lateral strips 622, 624 on a side of the plane including a base of jaw 614 as shown in FIGS. 19 and 20 such that when an Implant is received between the first and second gripper, the wing strips will press against the implant surface. Wing strips 623, 625 may have a maximum lateral span greater than an inner diameter of elongate housing 642. In such arrangements, the wing strips have flexible properties so that they deform upon being urged to be received within the lumen of elongate housing 642. In some examples, strips 622, 624, 626, 628 defining a central loop of the second gripper may be more rigid than wing strips 623, 625. To make the central loop more rigid than the wing strips, the material of the central loop may be thicker than the material of the wing strips.

Figure 21:
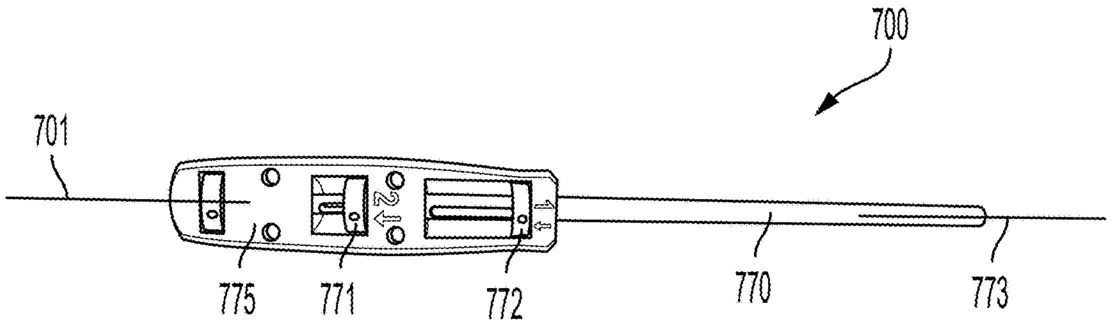
FIG. 21 is a top view of a delivery instrument according to one embodiment of the disclosure.
Figure 22:
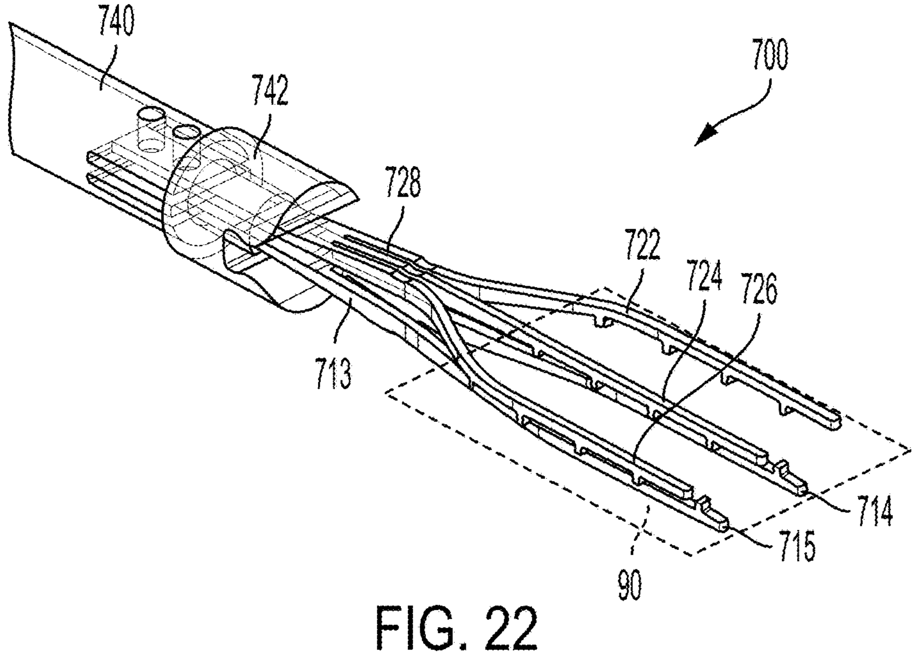
FIGS. 22 and 23 are perspective and side views, respectively, of a distal end portion of the delivery instrument of FIG. 21 in a deployed position.
Figure 23:
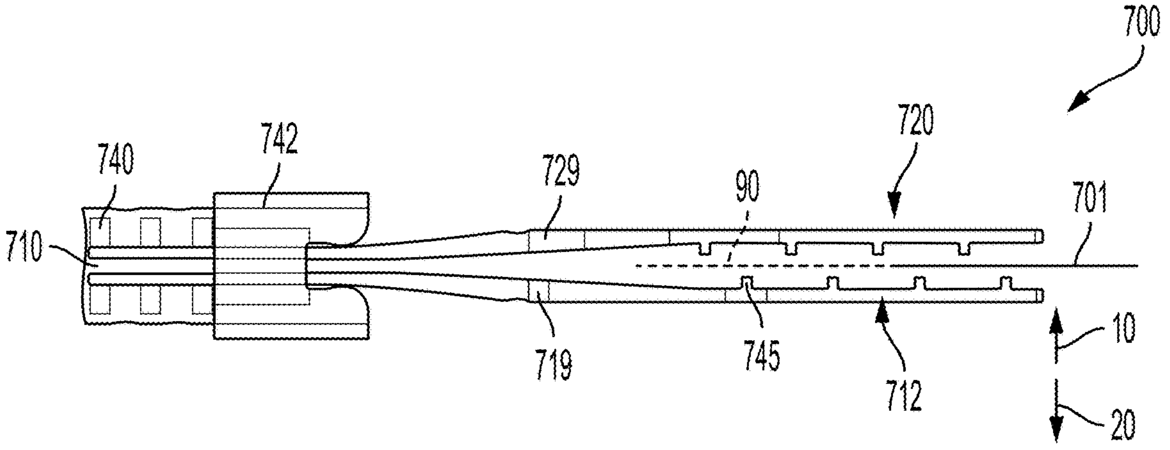

In other embodiments, a delivery instrument may include an implant engagement portion with a plurality of prongs to cover and engage with an implant. One such embodiment is delivery instrument 700 shown in FIGS. 21-26B. Delivery instrument 700 may include a handle 775 with an outer shaft 770 disposed therein, as shown in FIG. 21. Handle may also include controls 771, 772 for adjusting settings of the instrument. Such controls are described in greater detail below following a description of the various components of the instrument. Additional components of the instrument are disposed within the outer shaft and are shown in FIGS. 22 and 23. For case of reference, outer shaft 770 is not shown in FIGS. 22 and 23.

Disposed within outer shaft 770 is locking shaft 740 extending to a distal end with a bushing 742 attached thereto, as shown in FIGS. 22 and 23. Locking shaft is cannulated, and disposed within such cannulation is inner shaft 710. Inner shaft 710 extends to a distal end that is attached to an implant engagement portion, described further below. The series of three shafts are arranged such that outer shaft 770 is axially translatable relative to locking shaft 740 and inner shaft 710 along a central longitudinal axis 701 of instrument 700, and locking shaft 740 is axially translatable relative to outer shaft 770 and inner shaft 710 along the central longitudinal axis. Inner shaft 710 remains in a predetermined axial position relative to handle 775 of the instrument regardless of the position of the other shafts. In terms of operation, an axial position of bushing 742 is adjustable through sliding of block 771 within handle as shown in FIG. 21. And similarly, an axial position of outer shaft 770 is adjustable through sliding of block 772 as shown in FIG. 21. It should be appreciated that these controls are but one example and that other types of actuation mechanisms may also be included for adjustment of a position of locking shaft 740 and outer shaft 770.

Turning to the implant engagement portion extending distally from the inner shaft 710, the implant engagement portion includes a first gripper 712 and a second gripper 720 as shown in FIG. 23. Both first and second gripper extend distally from an end of inner shaft 710 and may be connected to inner shaft via a pin connection or other suitable connection. In a variation of delivery instrument 700, the first and second grippers could instead be attached directly to locking shaft 740 via a pin, protrusions and slots, other engagement features or a weld. In such variation, bushing 742 may be operatively connected with an additional longitudinally oriented shaft disposed over locking shaft 740 to control a position of bushing 742 on the delivery instrument. Returning to the depicted embodiment, first gripper 712 is positioned on a bottom side of the instrument while second gripper 720 is positioned on a top side. For case of reference, upward is indicated by reference numeral 10 and downward is indicated by reference numeral 20 in FIG. 23. As depicted, first gripper 712 includes a first base portion 713 extending from the inner shaft to an opposite end where the gripper splits into a pair of lower prongs 714, 715 as shown in FIG. 22. While these prongs are described as "lower," it should be appreciated that such characterization is not limiting on how delivery instrument may be used. In this way, it should be appreciated that the instrument may be used in the opposite orientation with the lower prongs being an upper side of the instrument. Over a length of base portion 713, first gripper is biased at a downward angle moving away from the inner shaft. Lower prongs 714, 715, as shown in FIG. 23, extend generally in parallel with central longitudinal axis 701. As each lower prong 714, 715 extends distally from base portion 713, such prongs spread apart as shown in FIG. 22. In variations, the first gripper may be a single jaw. In some examples of these variations, the single jaw may be fixed at all times while the second gripper changes position and shape based on actuation of the instrument. As to second gripper 720, a second base portion 728 extends from the inner shaft to an opposite end where the second gripper extends into a clamp covering a wider surface area. Such clamp may include a plurality of prongs which extend distally from the base portion. As depicted, the clamp includes three upper prongs 722, 724, 726. Similar to first gripper, second base portion 728 is biased at an upward angle moving away from the inner shaft, and upper prongs 722, 724, 726 extend generally in parallel with central longitudinal axis 701. One advantage of having upper prongs 722, 724, 726 is that when used to place an implant at a surgical site, staples or sutures may be dispensed onto the implant directly over one or more of the upper prongs while the upper prongs continue to press against the implant. Due to the shape of the upper prongs, delivery instrument 700 may be removed even after staples or sutures are dispensed according to methods of using delivery instrument 700. While these prongs are described as "upper," it should be appreciated that such characterization is not limiting on how delivery instrument may be used. In this way, it should be appreciated that the instrument may be used in the opposite orientation with the upper prongs being a lower side of the instrument.

Figure 31:
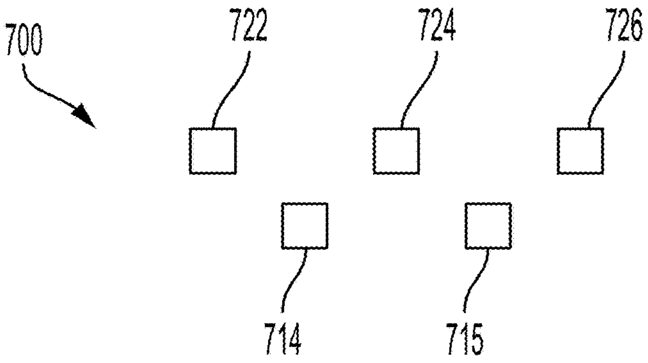
FIGS. 31-33 are sectional views of gripping prongs of a delivery instrument according to various embodiments of the disclosure.

For both lower and upper prongs, after an initial segment where the respective prongs spread apart laterally moving in a distal direction, each prong extends to a respective distal end generally in parallel with the other respective prongs. A cross-sectional view of the collective lower and upper prongs taken along a plane orthogonal to central longitudinal axis 701 is shown in FIG. 31. In some examples, one or both of first gripper and second gripper may include gripping protrusions 745 such as those shown in FIGS. 22 and 23. Other non-limiting examples of gripping features that may be included in implant-facing surfaces of the grippers include undulating surfaces and holes.

Figure 24A:
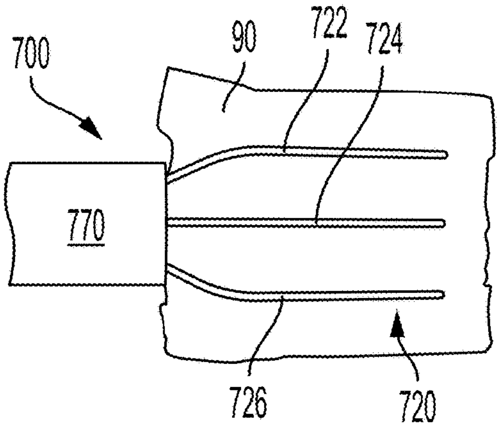
FIGS. 24A and 24B are top and bottom views, respectively, of the distal end portion of the delivery instrument of FIG. 21 in a deployed and unlocked position.
Figure 24B:
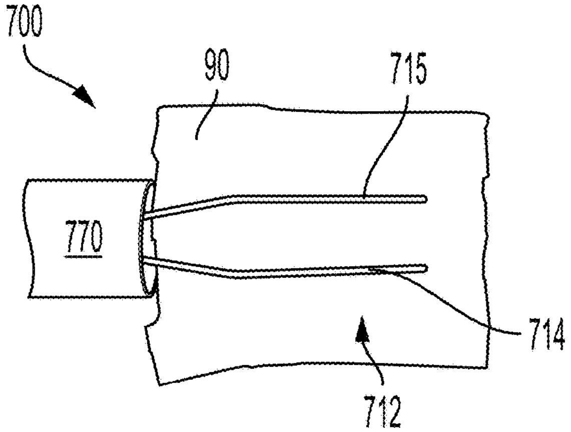
Figure 25:
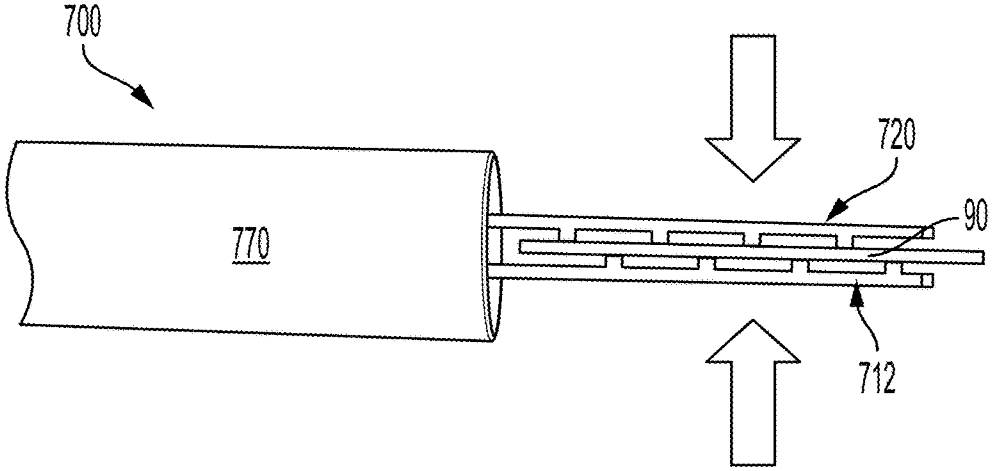
FIG. 25 is a side view of the distal end portion of the delivery instrument of FIG. 21 in a deployed and unlocked position.
Figure 26A:
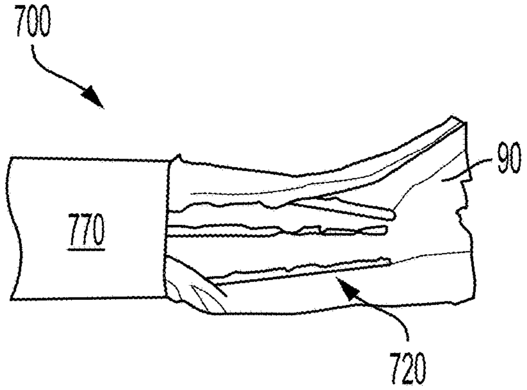
FIGS. 26A and 26B are top and bottom views, respectively, of the distal end portion of the delivery instrument of FIG. 21 in a partially enclosed and locked position.
Figure 26B:
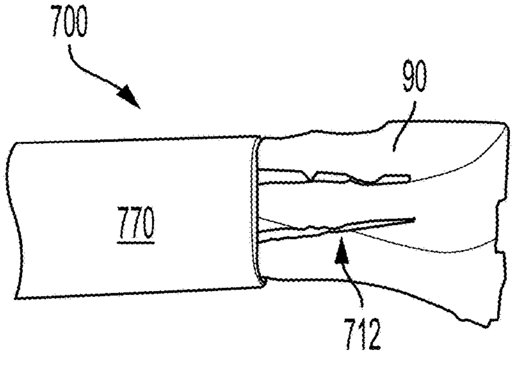

The operating mechanisms for delivery instrument 700 provide the following functions. Commencing from a condition where block 771 is in an unlocked position and block 772 is in a gripper-deployment position, an implant 90 may be received between first gripper 712 and second gripper 720, as shown from above in FIG. 24A and from below in FIG. 24B. Sliding of block 771 from the unlocked position to a locked position causes the respective grippers to close toward each other, thereby locking and holding implant 90 in between, as shown in FIG. 25. To stow the implant engagement portion, block 772 is slid from the gripper-deployment position to a gripper-enclosure position, as shown in FIGS. 26A and 26B, causing at least part of the lower prongs and at least part of the upper prongs to be drawn laterally closer to each other and become enclosed by outer shaft 770. Greater detail on the employment of such operative features as part of a method of using delivery instrument 700 is provided elsewhere in the present application.

In variations of delivery instrument 700, some examples may have a first gripper 712 with no bias while second gripper 720 is biased. In some examples, first gripper 712 may be biased while second gripper 720 is not biased. In still further examples, both first gripper 712 and second gripper 720 may have no bias in a neutral state. In such examples, delivery instrument 700 may include another mechanism to control gripping and releasing of the first and second grippers. Such mechanism may be actively controlled, in contrast to the passive control of first gripper 712 and second gripper 720 shown in FIGS. 21-26B. Further, while bias for either the first gripper or the second gripper of delivery instrument 700 is described as being at a downward angle or at an upward angle, it should be appreciated that the direction of bias for the respective grippers may be reversed such that the first gripper is biased at an upward angle toward a distal tip of the instrument while the second gripper is biased at a downward angle toward a distal tip of the instrument. Moreover, other examples are envisioned including where both the first gripper and the second gripper may be biased in a single direction, but to a different extent. In this way, elongate housing 742 may still operate to control gripping and release of the two grippers.

In other variations of delivery instrument 700, the prongs may have structure to provide the following performance characteristics. In some examples, the upper prongs and the lower prongs may be sized relative to the other components of delivery instrument 700 so that only the upper prongs move laterally toward and away from each other with actuation of block 772 from the gripper-deployment position to the gripper-enclosure position. In this manner, a shape of each lower prong and a spacing between each of the lower prongs remains the same regardless of the position of block 772. In other examples, the upper prongs and the lower prongs may be sized relative to the other components of delivery instrument 700 so that only the lower prongs move laterally toward and away from each other with actuation of block 772 from the gripper-deployment position to the gripper-enclosure position. In still further examples, a spacing of all prongs including both upper prongs and lower prongs may be constant in all operative positions of the delivery instrument.

In still further variations of delivery instrument 700, an additional cannulated shaft may be included in the instrument that is specifically designed to independently control the lateralization of the upper prongs, lower prongs, or both. This additional cannulated shaft may be axially translatable over at least inner shaft 710 to control lateral displacement of the applicable upper and/or lower prongs. In this manner, sliding of outer shaft 770 between a gripper-deployment position and a gripper-enclosure position would not affect a shape and spacing of any of the upper and lower prongs of the instrument. Put another way, an overall lateral width of the adjustable prongs from among the upper and lower prongs is controlled by a mechanism separate from outer shaft 770 used to control enclosure of such prongs.

While the above describes one arrangement of delivery instrument 700, it should be appreciated that the implant engagement portion may be varied in many ways. These include configurations such as those shown in FIGS. 27-34.

In some examples, the prongs of the first and second gripper may be configured to move in particular ways. In FIGS. 27-34, reference numerals refer to like elements in the 700-series of numerals for delivery instrument 700 unless otherwise indicated. In each of delivery instruments 700A-700D, the instrument may include an additional actuation mechanism to control a spacing of the prongs on the first or second gripper, a spacing of the first and second grippers themselves, or both. It should be appreciated that the features described for instruments 700A-700D are in addition to those already described as included in delivery instrument 700.

Figure 27:
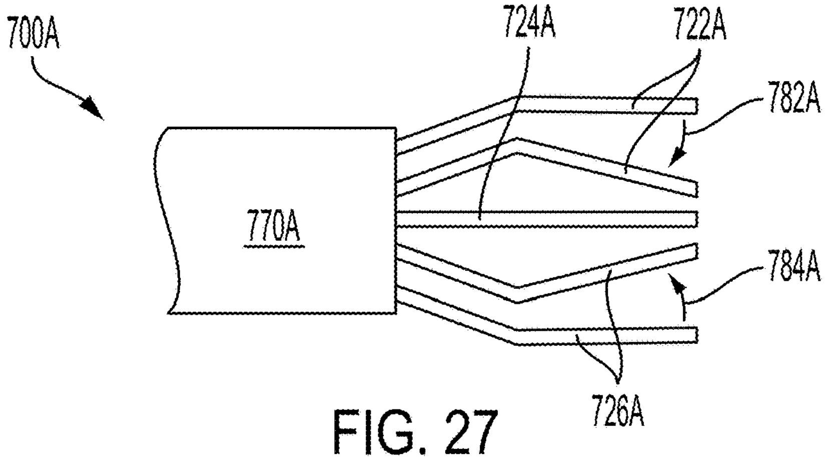
FIGS. 27-28 are top views of a delivery instrument according to various embodiments of the disclosure.
Figure 28:
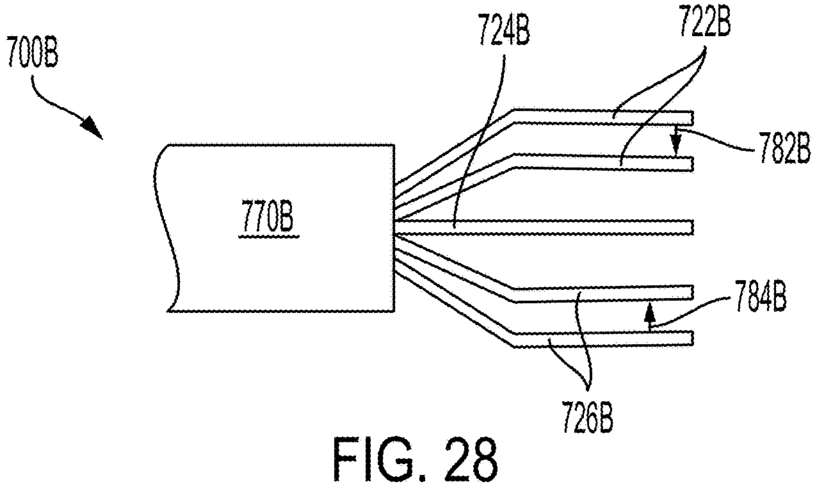
Figure 29:
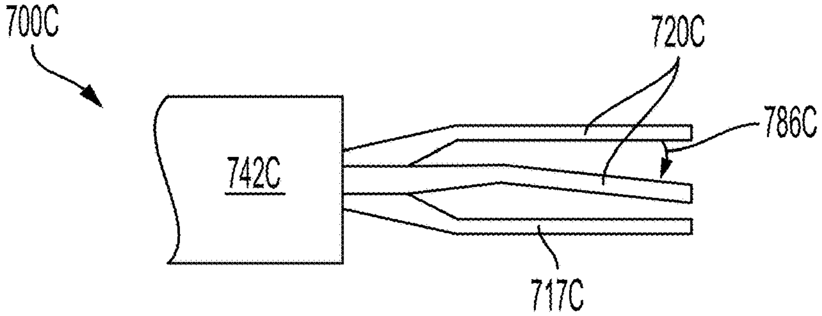
FIGS. 29-30 are side views of a delivery instrument according to various embodiments of the disclosure.
Figure 30:
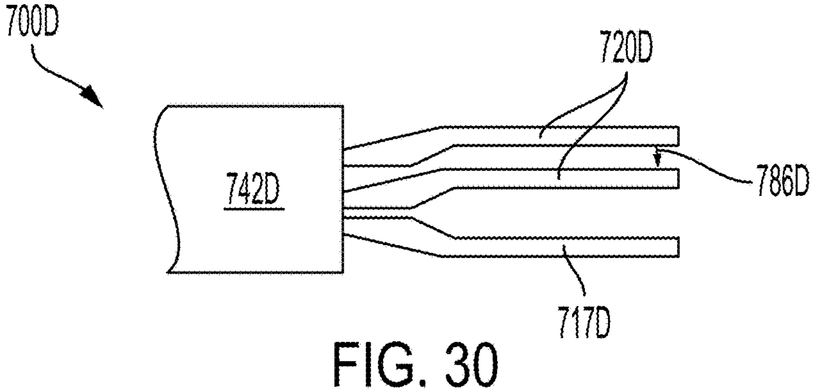

In FIG. 27, delivery instrument 700A as viewed from above includes a second gripper with upper prongs 722A, 724A, 726A. The instrument may include an additional actuation mechanism (not shown) that may be controlled to change a spacing between the upper prongs, here, by adjusting outer prongs 722A, 726A to move inward or outward in an arcuate movement as indicated by reference numerals 782A, 784A. This change in spread of the prongs may be used to account for different sized implants. It should be appreciated that in FIG. 27, three prongs are shown, but that the outer prongs are shown in two separate locations to indicate a path of movement. The instruments in FIGS. 28-30 are similarly depicted, where three prongs are shown in FIG. 28 and two grippers are shown in each of FIGS. 29 and 30. In FIG. 28, delivery instrument 700B as viewed from above includes a second gripper with upper prongs 722B, 724B, 726B. The instrument may include an additional actuation mechanism (not shown) that may be controlled to change a spacing between the upper prongs, here, by adjusting outer prongs 722B, 726B to move inward or outward in a parallel movement as indicated by reference numerals 782AB, 784B. In variations of the above-described embodiments, size, quantity and spacing of the prongs may be modified to obtain a desired surface area coverage for an implant and in this manner the particular arrangements depicted in FIGS. 27 and 28 are not limiting.

In FIG. 29, delivery instrument 700C, as viewed from the side, includes a first gripper with a fixed lower jaw 717C and a second gripper 720C. The instrument may include an additional actuation mechanism (not shown) that may be controlled to change a spacing between fixed lower jaw 717C and second gripper 720C by rotating second gripper 720C along an arcuate path toward the fixed lower jaw 717C. Such adjustments in the unlocked, open position of the grippers may be made to alter the degree of pressure applied to an implant received by the instrument when the grippers are locked. Similarly, in FIG. 30, delivery instrument 700D, as viewed from the side, includes a first gripper with a fixed lower jaw 717D and a second gripper 720D. The instrument may include an additional actuation mechanism (not shown) that may be controlled to change a spacing between fixed lower jaw 717C and second gripper 720C by translating second gripper 720C toward fixed lower jaw 717C while remaining parallel to fixed lower jaw 717C.

Figure 32:
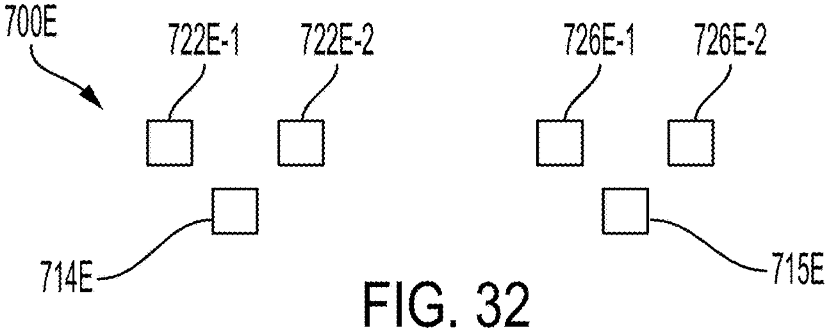
Figure 33:
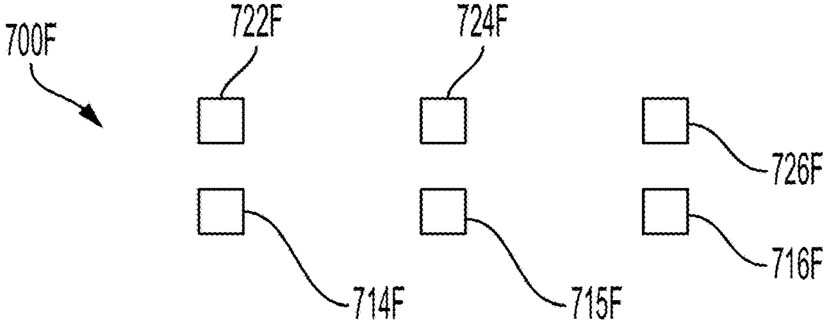

In some examples, the prongs of the implant engagement portion may be arranged in various ways to accommodate a desired coverage of surface area for contact with an implant held by the delivery instrument (e.g., implant 90 shown in FIG. 16). In FIG. 32, delivery instrument 700E may include two lower prongs 714E, 715E spread apart from each other, where each of those lower prongs correspond to a respective pair of upper prongs 722E-1, 722E-2 and 726E-1, 726E-2. In this manner, the pairs of upper prongs are spaced at a similar distance from each other as the two lower prongs. In FIG. 33, an implant engagement portion of delivery instrument 700F includes three lower prongs 714F, 715F, 716F and three upper prongs 722F, 724F, 726F. In this arrangement, the prongs form a symmetrical arrangement as viewed in section and are laterally spaced in an equal manner, such that the upper and lower prongs are directly opposed to one another. Of course, the arrangements of FIGS. 31-33 are merely illustrative, and it is contemplated that the prongs may be arranged in other ways consistent with the examples provided in this disclosure.

Figure 34:
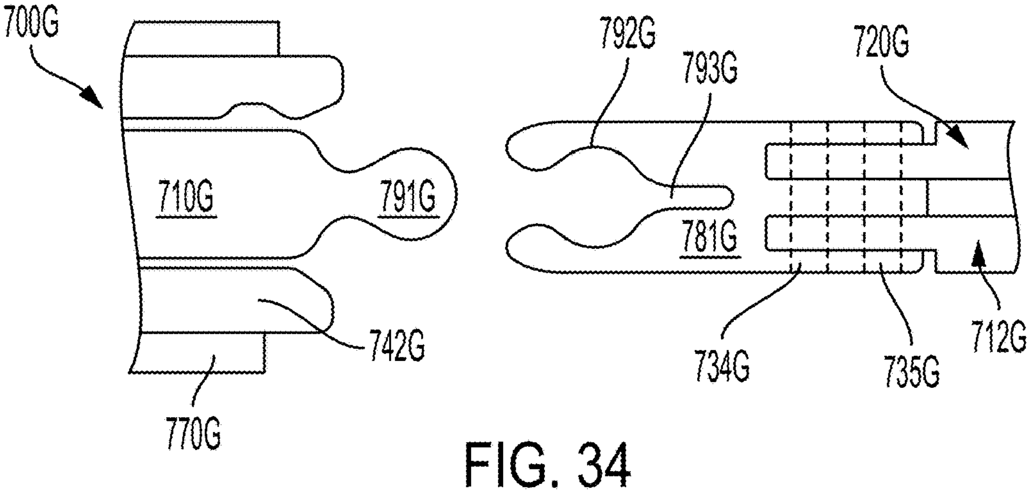
FIG. 34 is a side view of a connection feature of a delivery instrument according to one embodiment of the disclosure.

In still further examples, delivery instrument 700, including the numerous explicit example variations contemplated herein, may be modified to have a modular implant engagement portion such that different implant engagement portions may be attached to the main body of the instrument. This is one way to provide an instrument that can grip implants of a wide variety of sizes. Using a modular approach, some exemplary arrangements may provide for use of the instrument to receive implants ranging in size from 10 mm to 30 mm, for example. One example of the modular implant engagement portion is shown as part of delivery instrument 700G in FIG. 34. Inner shaft 710G extends to a distal end including a ball 791G forming a ball of a ball-and-socket joint. In addition to features in common with other embodiments described herein, such as bushing 742G and outer shaft 770G, delivery instrument 700G also includes an adapter 781G, as shown in FIG. 34. Adapter is configured to provide a bridge between a distal end of inner shaft 710G and the first and second gripper at the distal end of the instrument. Adapter includes, at one end, a socket 792G with a distally extending slit 793G. The inclusion of the slit allows for the arms surrounding the socket to elastically expand temporarily to snap over ball 791G to engage adapter to inner shaft 710F. Adapter may also include one or more channels to receive pins 734G, 735G to secure lower gripper 712G and upper gripper 720G to the adapter. In some examples, another form of securement to provide a fixed connection between the grippers and the adapter may be used.

Additionally, delivery instrument 700 may be varied in other ways as well. For instance, in some examples, first gripper 712 may include a single jaw extending from the base. In some examples, whether first gripper is a plurality of prongs or a single jaw, such first gripper may be a fixed structure such that axial translation of the locking shaft or the outer shaft does not cause upward or downward movement of the first gripper.

Figure 35A:
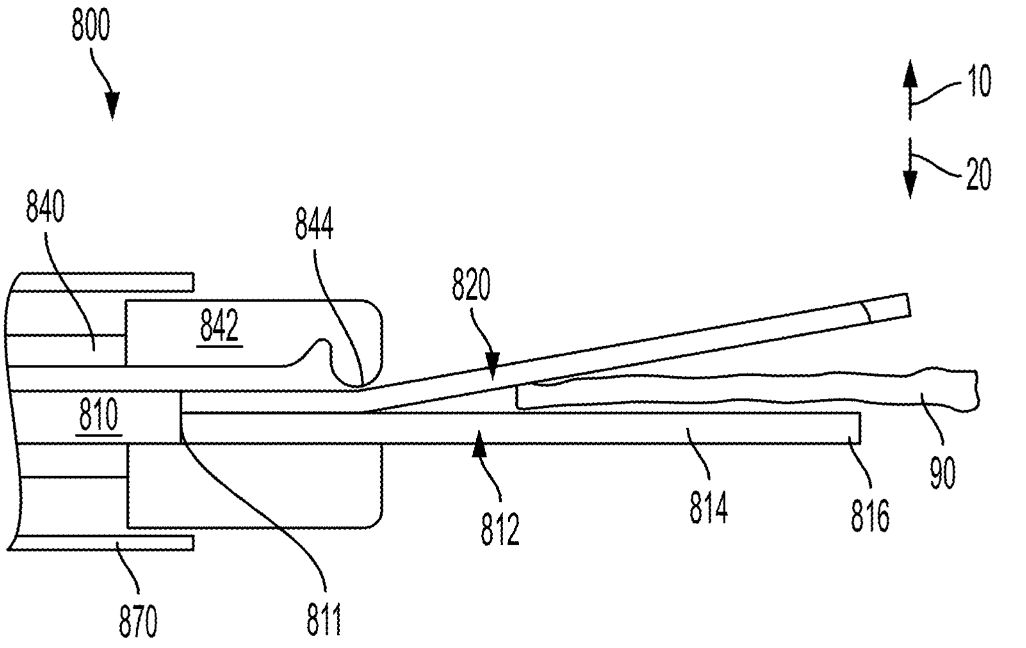
FIGS. 35A-35B are side and top views, respectively, of a delivery instrument according to one embodiment of the disclosure.
Figure 35B:
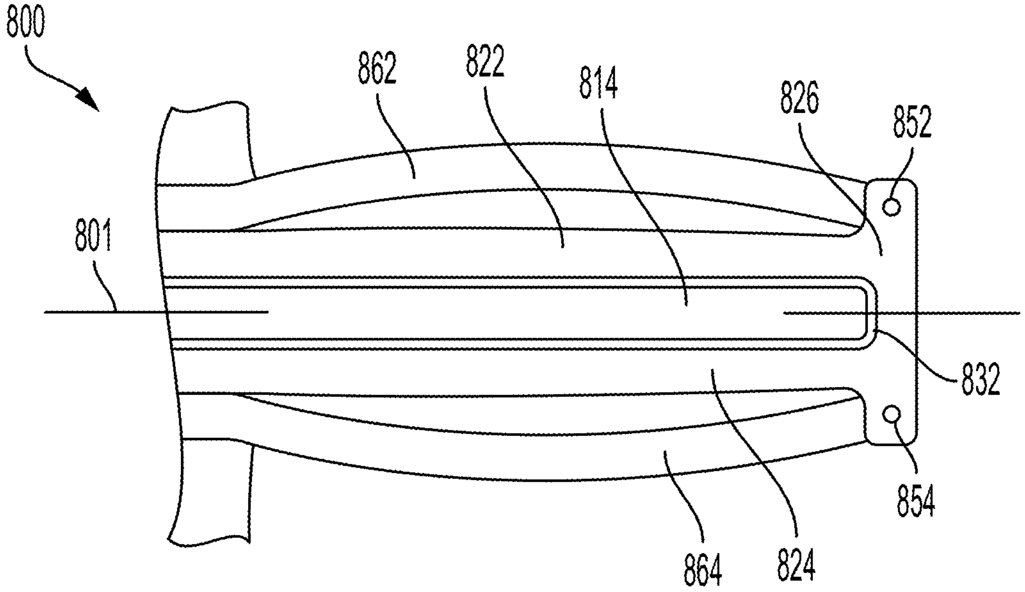

In yet another embodiment, delivery instrument 800 is shown in FIGS. 35A and 35B. Reference numerals in the 800-series of numerals for delivery instrument 800 refer to like elements in the 100-series of numerals for delivery instrument 100 unless otherwise indicated. For ease of reference, upward is indicated by reference numeral 10 and downward is indicated by reference numeral 20 in FIGS. 35A and 36A. While reference may be made to upper, top, lower or bottom sides of delivery instrument 800, it should be appreciated that such directional references for the instrument are not limiting, and that it is contemplated that the instrument may be used when oriented in a manner such that those directional references may apply in a different way. For example, if the instrument is held in an opposite manner such that a first gripper 812 is above a second gripper 820.

Delivery instrument 800 includes a central implant gripper, a lateral spreading mechanism and a gripper-locking mechanism. In some variations, delivery instrument 800 may also include an outer shaft. A distal end region of the delivery instrument includes the features configured to interact directly with an implant, such as an augment. The distal end region is depicted in FIGS. 35A-36B. At a proximal end region of the delivery instrument opposite the distal end region, controls (not shown) are included for manipulation of the instrument. In some examples, the instrument may have three separate controls while in other examples the instrument may have two of the three separate controls. One of these controls is a mechanism to cause axial translation of a central wing shaft thereby causing lateral wings to move laterally outward or inward relative to a central longitudinal axis 801 of the instrument. Another control causes axial translation of a locking shaft thereby closing or opening gripper elements at a distal portion of the central implant gripper. Additionally, yet another control causes axial translation of an outer shaft to either advance the outer shaft over an entirety of the distal portion of the central implant gripper or to retract the outer shaft to expose varying degrees of the distal portion of the central implant gripper. In some examples, these controls may simply be the holding of an applicable shaft and sliding it axially relative to the central implant gripper. In other examples, controls may be provided through additional instrument components such as slidable switches or rotatable wheels. Further detail respecting the central implant gripper, lateral spreading mechanism, gripper-locking mechanism, and other features of the delivery instrument will now be described.

Figure 36A:
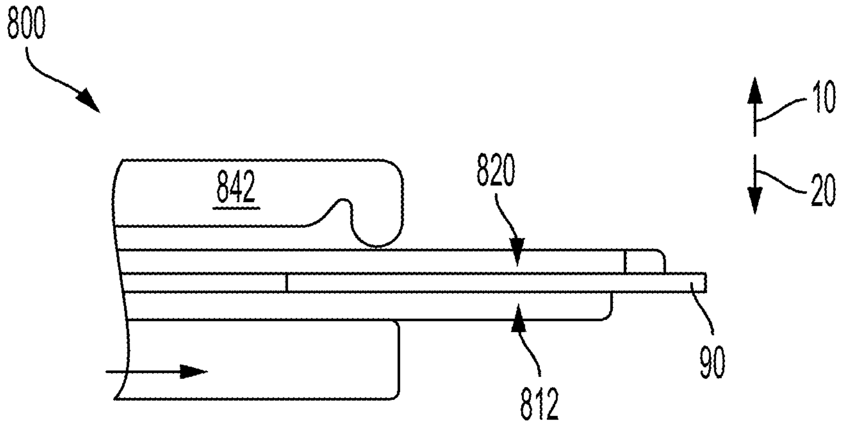
FIGS. 36A-36B are side and top views, respectively, of a delivery instrument according to one embodiment of the disclosure.

As to the central implant gripper of the instrument, the central implant gripper forms a base structure of the instrument that is axially static while other parts of the instrument are actuated. The central implant gripper includes a base shaft 810 that extends along central longitudinal axis 801 from the proximal end region of the instrument to a distal end 811 abutting both a first gripper 812 and a second gripper 820. Both the first and second gripper are attached to the distal end of the base shaft. In some examples, base shaft 810, first gripper 812 and second gripper 820 may be a monolithic structure. In other examples, two of the base shaft, first gripper and second gripper may be monolithic. First gripper 812 is attached below second gripper 820, as shown in FIGS. 35A and 36A, where "below" is used to reference a side of the instrument facing downward as indicated by reference numeral 20 in FIG. 35A. First gripper 812 includes a jaw 814 that extends to a tip 816 at a free end. Jaw 814 may be fixed relative to central shaft 810 so that it remains static relative to the central shaft during use of the delivery instrument including in instances when controls are operated. Second gripper 820 includes a central body that extends distally from distal end 811 of the base shaft. The central body includes a pair of strips extending along the central longitudinal axis, i.e., a first lateral strip 822 and a second lateral strip 824, and an end strip 826 bridging the two lateral strips proximate a distal end of the lateral strips, as shown in FIG. 35B. These strips define a closed loop with an opening 832 therebetween. As shown, second gripper 820 is biased such that when in a neutral state, i.e., when bushing 842 is retracted as shown in FIG. 35A, the second gripper is oriented upward and away from the first gripper moving distally toward a distal tip of the delivery instrument. Put another way, a distance between the second gripper and the first gripper progressively increases from a location proximate the bushing toward a distal end of the respective grippers. When force is applied to a top surface of the second gripper, as may occur when bushing 842 is slid distally over the second gripper, the second gripper is pushed downward and toward the jaw of the first gripper. Further detail regarding the operation of bushing 842 is described elsewhere in the application.

While the figures show second gripper 820 as biased and first gripper 812 as static, it is contemplated that the instrument may be arranged in an opposite manner, such that the first gripper is biased away from the second gripper in a neutral state while the second gripper remains static irrespective of whether bushing 842 is retracted or extended. In such arrangements, the second gripper may be fixed relative to central shaft 810. And, in further alternatives, both first gripper 812 and second gripper 820 may be biased away from each other. In any of the above examples, a biasing feature may be substituted with another similar feature that allows a movable gripper to pivot. In other alternatives, both first gripper 812 and second gripper 820 have no bias in a neutral state. In such arrangements, delivery instrument 800 may include another mechanism to control gripping and releasing of the first and second grippers. Such mechanism may be actively controlled, in contrast to the passive control of a separation between first gripper 812 and second gripper 820 in FIG. 35A via bushing 842.

Figure 36B:
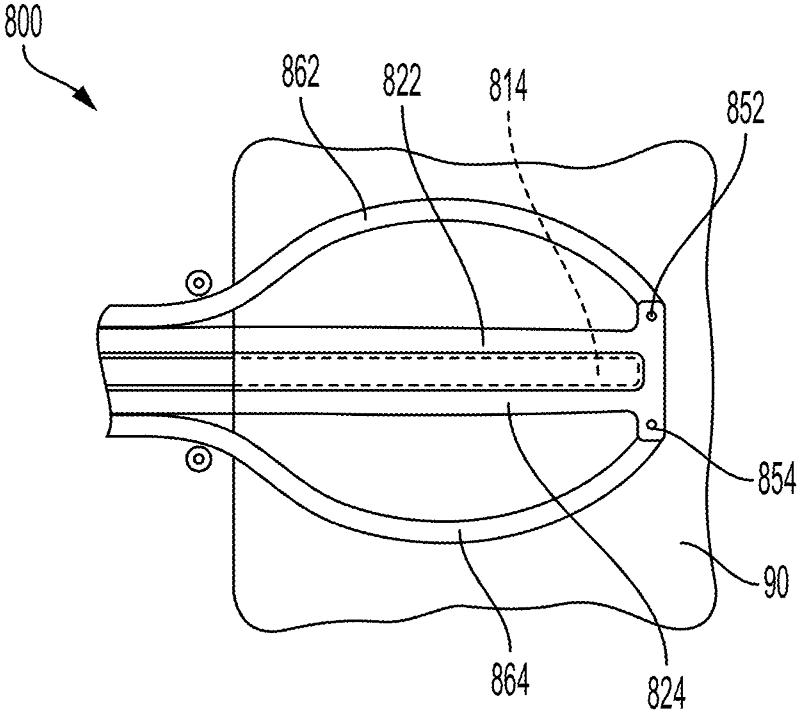
Figure 37:
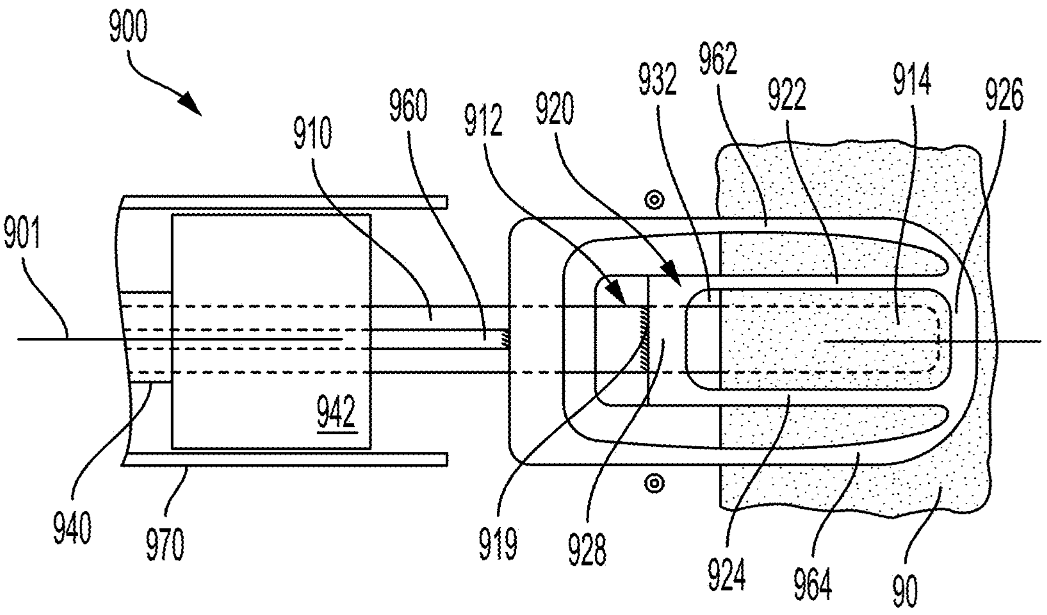
FIG. 37 is a top view of a delivery instrument according to one embodiment of the disclosure in a first position.
Figure 38:
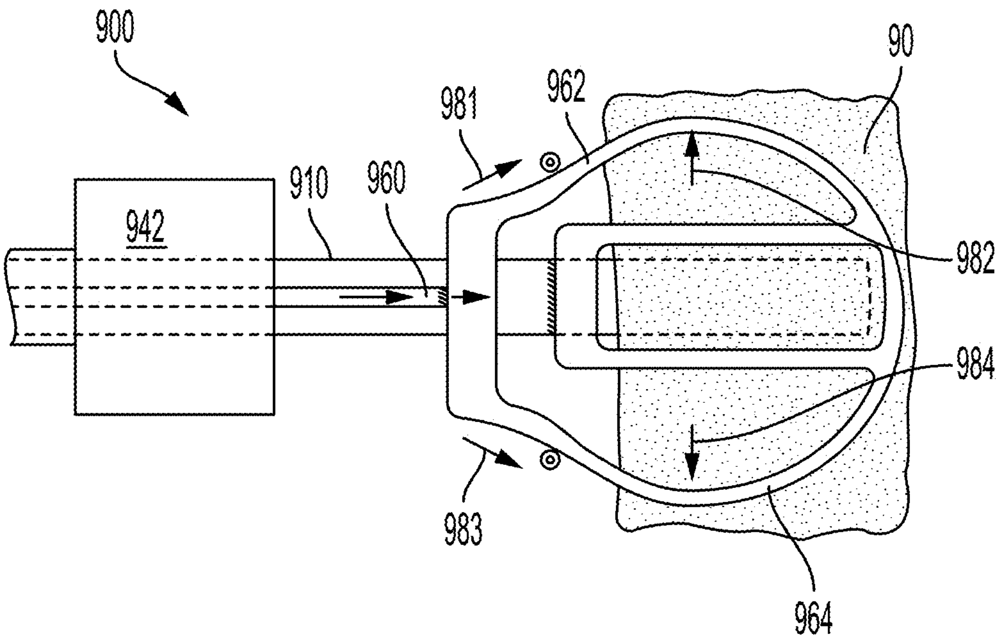
FIG. 38 is a top view of the delivery instrument of FIG. 37 in a second position.

As to the mechanism for lateral spreading of an implant at the distal end of delivery instrument 800, also referred to as a "lateral spreading mechanism," and "a first actuation assembly," the instrument includes a central wing shaft (not shown), but similar to central wing shaft 960 shown in FIGS. 37 and 38) extending generally parallel to base shaft 810 along a length of the instrument. In the distal end region of the instrument, the central wing shaft is operatively connected to first lateral wing 862 on a first side of the pair of grippers and a second lateral wing 864 on a second side of the pair of grippers, the second side being opposite the first side, as shown in the top-down view of FIG. 35B, for example. While shown and described as having two lateral wings, in some alternative examples, the instrument may include a single lateral wing. Each lateral wing 862, 864 has a length extending from the central wing shaft to a distal end or a location proximate the distal end of the central body of second gripper 820. In the depicted embodiment in particular, pins 852, 854 are disposed at opposite sides of end strip 826 of the second gripper, and distal ends of the respective lateral wings 862, 864 are connected to end strip 826 via respective pins 852, 854. In this manner, each lateral wing is pivotable relative to the end strip. In a neutral position, each lateral wing 862, 864 is slightly buckled outward away from the central body of second gripper 820, as shown in FIG. 35B. Such a configuration ensures that each lateral wing moves laterally outward from a neutral position when the central wing shaft is advanced distally. Thus, through axial advancement of the central wing shaft, each lateral wing 862, 864 buckles further outward, as shown in FIG. 36B. A control of the lateral wings may be configured to adjust the lateral wings in predetermined increments or gradually, such as through incorporation of a dial or wheel as a control. To avoid ambiguity, it should be appreciated that in the contemplated arrangements of the instrument, the wings are operated separately from central shaft 810. Further details regarding the operation of delivery instrument are described elsewhere in the present disclosure.

With reference now to components of the instrument disposed over and housing the central implant gripper and the lateral spreading mechanism, delivery instrument also includes a gripper-locking mechanism, also referred to as a "second actuation assembly," with a locking shaft 840 and a bushing 842 attached at its distal end. In some examples, the locking shaft and the bushing may form part of a monolithic structure. The gripper-locking mechanism includes a lumen therethrough for passage of the base shaft and the central wing shaft therethrough. In some examples, the gripper-locking mechanism, and bushing 842 in particular, controls closure and opening, i.e., locking and unlocking, of the first and second grippers. Bushing 842 may be a generally tubular shaped structure and may have a lumen therethrough with a constant or varying diameter along its length. In some examples, a distal opening of the lumen of bushing 842 may include a neck 844 feature where the opening is narrowed, as shown in FIG. 35A. Such configuration may be used to provide a tighter closure of the first and second grippers when the bushing is slid over the grippers. And, to the extent lesser or greater pressure between the grippers in the closed position is sought, neck 844 dimension may be modified, with larger sized necks applying less pressure when passed over the grippers.

In some variations, delivery instrument 800 may further include an outer shaft 870 disposed over the gripper-locking mechanism such that the gripper-locking mechanism passes through a lumen of the outer shaft 870. Outer shaft 870 may be axially translatable along the central longitudinal axis of the instrument between a retracted position and an extended position to control deployment and enclosure of the distal end region of the instrument, including the grippers and lateral wings.

In another embodiment, delivery instrument 900 is shown in FIGS. 37 and 38. Reference numerals in the 900-series of numerals for delivery instrument 900 refer to like elements in the 800-series of numerals for delivery instrument 800, unless otherwise noted. As with delivery instrument 800, delivery instrument 900 includes a central implant gripper, a lateral spreading mechanism and a gripper-locking mechanism. Central implant gripper includes first gripper 912 and second gripper 920. As shown in FIGS. 37 and 38, first and second grippers are attached proximate an attachment region 919. Such attachment may be through various means known to those of skill in the art, such as through a weld or a fastener. One of first gripper 912 and second gripper 920 may be biased away from the other of the first gripper and the second gripper when in a neutral state so that an implant, such as implant 90 shown in FIGS. 37-38, may be advanced into a space between the grippers. First gripper includes jaw 914 extending along a central longitudinal axis 901 of the instrument, and second gripper 920 includes a central body with a series of strips defining an opening 932 therein, the central body also generally extends along the central longitudinal axis. As depicted in the figures, the central body includes a base strip 928, first lateral strip 922, second lateral strip 924, and end strip 926, all forming part of a monolithic structure. Further, first and second lateral wings 962, 964 of the lateral spreading mechanism are also monolithically formed with the central body in the depicted embodiment. While the connection of the lateral wings and the central body are different in delivery instrument 900 compared to delivery instrument 800, the operative function of the instrument is the same. That is, central wing shaft 960 may be axially translated distally and proximally to control an extent of lateral displacement of lateral wings 962, 964. One example of this is shown through a comparison of FIGS. 37 and 38, where the lateral wings are withdrawn toward the central longitudinal axis in FIG. 37, and are pushed forward, as indicated by reference numerals 981 and 983, and laterally displaced outward from the central longitudinal axis, as indicated by reference numerals 982 and 984, in FIG. 38. Put another way, the lateral wings buckle outward as central wing shaft 960 is advanced. In some examples, distal end regions of wings 962, 964 may be thinner than other parts of the wings and the adjacent end strip 926. In this way, the lateral spreading mechanism in such examples may have a living hinge at the distal ends of the wings to emulate the performance characteristics of pin connections to the end strip without the inclusion of pins.

It should be appreciated that while FIGS. 37 and 38 illustrate a base-type transition structure between central wing shaft 960 and lateral wings 962, 964, which is axially translatable in conjunction with translation of the shaft, in other examples, the central wing shaft may be connected to proximal ends of the lateral wings that are oriented in parallel with the central wing shaft such that there is no transition structure. One such arrangement is provided in delivery instrument 1000, described below.

In yet another embodiment, delivery instrument 1000 is shown in FIGS. 39-46. Reference numerals in the 1000-series of numerals for delivery instrument 1000 refer to like elements in the 800-series of numerals for delivery instrument 800 unless otherwise indicated. Delivery instrument 1000 includes a base shaft 1010 with a first gripper 1012 and second gripper 1020 extending from a distal end thereof. Additionally, delivery instrument includes lateral wings 1062, 1064 attached to a distal end of second gripper 1020 and operatively connected to a thumb wheel control 1078 via a central wing shaft 1060 within a handle 1075 of the instrument. Disposed over base shaft 1010 and the operative mechanism for the lateral wings is bushing 1042, slidably disposed thereon. Bushing 1042 is axially translatable through sliding of control button 1071 in handle 1075. Further, disposed over the aforementioned components is outer shaft 1070, axially translatable via sliding of control button 1072 on handle 1075. Outer shaft 1070 may be axially translated to control whether a distal end portion of the outer shaft encloses the grippers and wings or deploys the grippers and wings. Positioning of controls 1071 and 1072 is such that when control button 1072 moves outer shaft 1070 into a gripper-enclosure position enclosing the gripper elements, control 1071 must remain in the locked position until control 1072 is returned to the gripper-deployment position.

The delivery instrument may be varied in many ways. While delivery instruments 800, 900, 1000 provide an "alligator" type opening and closing of grippers, such as first and second grippers 812, 820, it is contemplated that such grippers may be moveable in parallel with respect to each other when moving the instrument between the unlocked and locked positions. Further, the implant engagement portions of the other delivery instruments contemplated by the present disclosure, such as that included in delivery instrument 100, for example, may be substituted in place of the grippers of delivery instrument 800. In this way, a delivery instrument could include the lateral wings of instrument 800 and have the gripping features of instrument 100. Such combinations of the various embodiments of the disclosure are contemplated for all embodiments of the present disclosure.

Figure 49:
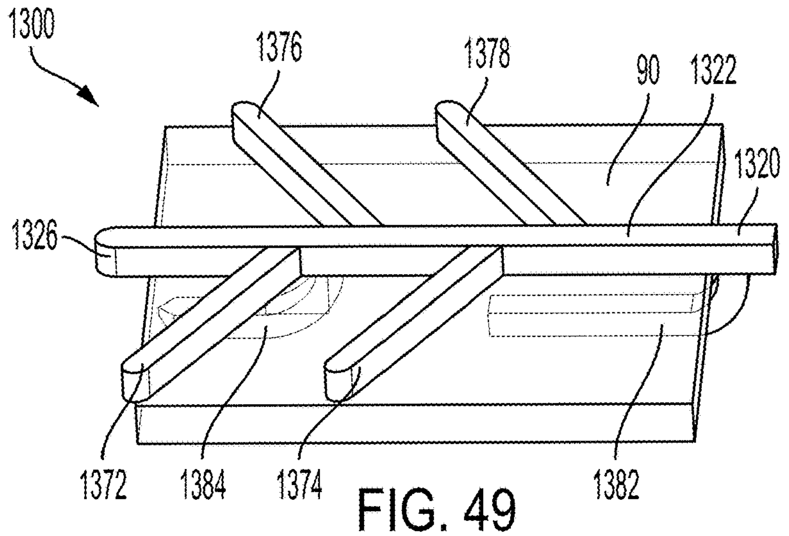
FIGS. 49-51 are partial perspective views of respective delivery instruments according to embodiments of the disclosure.
Figure 50:
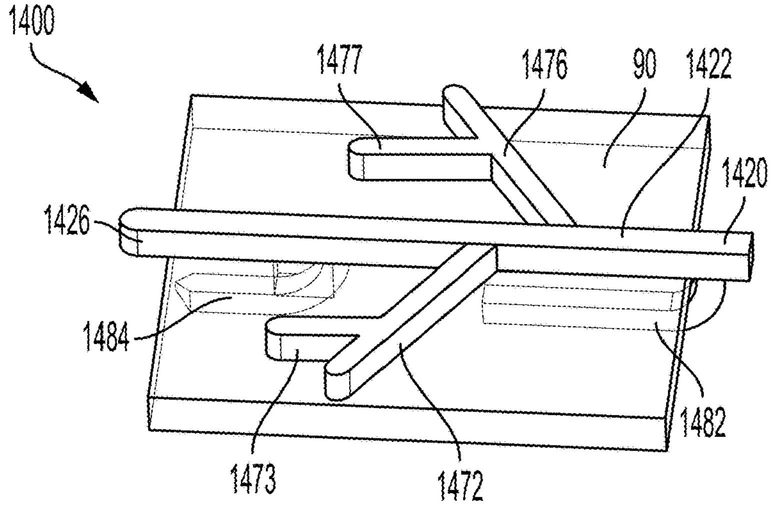
Figure 51:
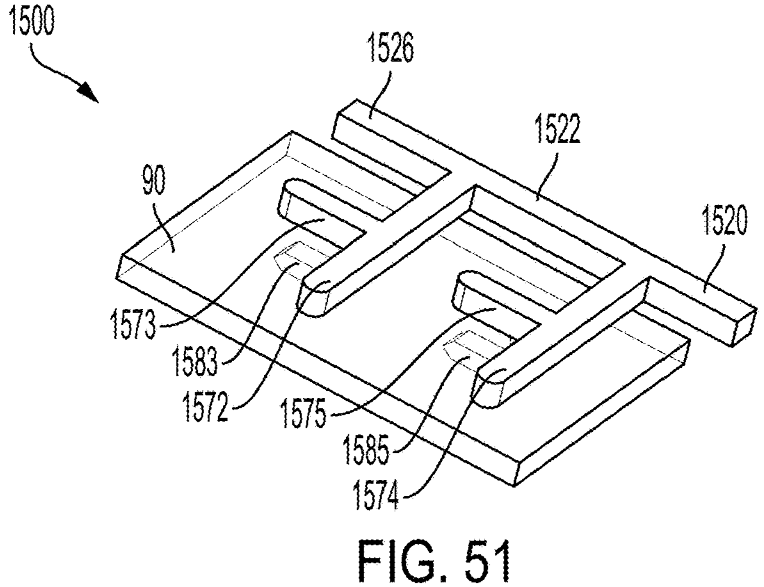

In still further embodiments, a delivery instrument may be as shown in FIGS. 49-51. Specifically, delivery instrument 1300 is shown in FIG. 49, delivery instrument 1400 is shown in FIG. 50, and delivery instrument 1500 is shown in FIG. 51. For each of delivery instrument 1300, 1400, 1500, reference numerals in the respective 1300, 1400 and 1500-series of numerals refer to like elements in the 300-series of numerals for delivery instrument 300 unless otherwise indicated. As with delivery instrument 300, delivery instruments 1300, 1400, 1500 include a central shaft (not shown) with an implant engagement portion attached thereto and an elongate housing (not shown) slidable over the central shaft to control exposure of the implant engagement portion. The elongate housing may extend from an outer shaft.

Turning to delivery instrument 1300, the implant engagement portion includes a gripper 1320 that extends to a tip 1326 remote from the central shaft. Gripper 1320 includes a plurality of branches 1372, 1374, 1376, 1378 distributed along a length of gripper 1320. As depicted in FIG. 49, two branches 1372, 1374 are on a first side of a trunk 1322 of gripper 1320 and another two branches 1376, 1378 are on a second side of trunk 1322 opposite the first side. The pair of branches 1372, 1374 on the first side is offset from the pair of branches 1376, 1378 on the second side along the length of trunk 1322. Each branch 1372, 1374, 1376, 1378 has an elongate dimension that extends at an acute angle relative to a central axis of trunk 1322 of gripper 1320. Branches 1372, 1374, 1376, 1378 are oriented such that each branch becomes further from a base of gripper 1320 toward a free end of the branch. Gripper 1320 also includes prongs 1382, 1384 extending from trunk 1322 in a direction generally orthogonal to a direction of extension of branches 1372, 1374, 1376, 1378 from trunk 1322. Put another way, bodies of prongs 1382, 1384 and trunk 1322 may pass through a first plane that is generally orthogonal to a second plane that passes through branches 1372, 1374, 1376, 1378 and trunk 1322. Each prong 1382, 1384 extends away from trunk 1322 at its base and curves further along its length so that a portion of each prong 1382, 1384 is generally parallel to trunk 1322. Gripper 1320 may be partially or entirely formed of flexible materials, such as nitinol. In use, branches 1372, 1374, 1376, 1378 are configured to spread apart an implant, such as implant 90, i.e., to keep implant 90 from being crumpled while gripper 1320 is exposed from the elongate housing. Prongs 1382, 1384 are configured to be positioned through, e.g., punctured through an implant so that the implant, such as implant 90, may be held in between the branches 1372, 1374, 1376, 1378 and the prongs 1382, 1384.

Delivery instrument 1400 has an implant engagement portion that includes a gripper 1420. Gripper 1420 includes a trunk 1422 that extends from a base to a tip 1426, branches 1472, 1476 extending from trunk 1422 and prongs 1482, 1484 also extending from trunk 1422. Branch 1472 extends from a first side of trunk 1422 and branch 1476 extends from a second side of trunk 1422 opposite the first side. Branches 1472, 1476 are offset from each other along a length of trunk 1422 and both have an elongate dimension that is at an acute angle relative to trunk 1422. Additionally, each branch 1472, 1476 includes an extension portion proximate a free end of the respective branches 1472, 1476. Branch 1472 includes extension portion 1473 and branch 1476 includes extension portion 1477. Each extension portion 1473, 1477 has an elongate dimension that is generally parallel to trunk 1422. As depicted, extension portion 1473 is shorter than extension portion 1477. In variations, an absolute length of either extension portion may vary from that shown in FIG. 50 and/or a relative length of the extension portions may also vary. Prongs 1482, 1484 are similar to those of delivery instrument 1300 and extend from trunk 1422 in a direction orthogonal to a direction of extension of branches 1472, 1476. Prongs 1482, 1484 include respective portions that are generally parallel to trunk 1422. Functions of the components of delivery instrument 1400 are similar to those described for delivery instrument 1300.

Delivery instrument 1500 has an implant engagement portion that includes a gripper 1520. Gripper includes a trunk 1522 that extends to a tip 1526. Gripper 1520 also includes two branches 1572, 1574, each extending from the same side of branch 1522. In this manner, gripper 1520 is asymmetric about an axis of trunk 1522 and only includes branches on one side of trunk 1522. As depicted, each branch 1572, 1574 extends approximately perpendicularly from trunk 1522. Further, each branch 1572, 1574 includes an extension portion 1573, 1575 that is oriented approximately parallel to trunk 1522. For each branch 1572, 1574, branch 1572, 1574 and extension portion 1573, 1575 are arranged so that a single plane passes through both in a neutral position. Each branch 1572, 1574 also includes a respective prong 1583, 1585. Each prong 1583, 1585 extends away from branch 1572, 1574 in a direction away from the aforementioned single plane, then curving to a portion that extends parallel to the extension portion 1573, 1575 on the branch 1572, 1574. In variations, an exact orientation of one or both branches 1572, 1574 relative to trunk 1522 may vary relative to that shown in FIG. 51. Similarly, in variations, an orientation of one or more extension portions 1573, 1575 and/or prongs 1583, 1585 relative to branches 1572, 1574 may be different from that shown in FIG. 51. Functions of the components of delivery instrument 1500 are similar to those described for delivery instrument 1300.

In another aspect, the present disclosure relates to a kit of instruments. In one embodiment, the kit may include two or more delivery instruments of the same embodiment of the delivery instrument. These may be the same or different sizes. In other embodiments, the kit may include at least two different delivery instruments, each being a distinguishable embodiment. In a subset of these examples, at least two of the delivery instruments included in the kit may be of the same embodiment. In any of the above embodiments, a kit may further include an instruction manual with an explanation of details relating to the contents of the kit including instructions for use of the contents. Further, in any of the above embodiments, a kit may include an implant, such as a graft. Materials used in conjunction with the implants may also be included as part of a kit as contemplated by the present disclosure. Such materials may include, for example, human collagen, bovine collagen, xenograph collagen, a synthetic material, a polyester material, an absorbable material, an organic material, silk, or combinations thereof.

In another aspect, the present disclosure relates to methods of manufacturing a delivery instrument. In some embodiments, the delivery instrument may be manufactured using machining techniques. In some embodiments, laser technology may be used to form the components that are assembled into a delivery instrument.

In yet another aspect, the present disclosure relates to a method of using a delivery instrument to deliver an implant to a surgical site. In some examples, a surgical site may be one of the tendons or muscles of a human rotator cuff. A surgery on the tissue of the tendon or muscle may be required to remedy deterioration due to disease, damage or injury. To facilitate the remedy via a repair, one solution is to secure an implant such as a tissue augment to the targeted portion of the tissue. The tissue augment may be a graft. In the description of the methods below, references are made to a "user." A "user" may be any user of the delivery instrument, such as a medical professional.

In one embodiment, delivery instrument 100 is used to perform a surgical procedure to repair a tendon of the rotator cuff at a target site where the implant is preloaded in elongate housing 142 of instrument 100, as shown in FIG. 5. Such preloading may be completed at the time of assembly of the instrument and as such a user of the instrument need not load an implant, such as implant 90, into the instrument in an intraoperative setting. Preloading at a manufacturing site also avoids the need to consider use of funnel 150. From these starting conditions, access to a target site in a patient is created. This procedure may be minimally invasive in that access may be provided through a cannula, i.e., tube shaped device, having a diameter that minimizes disruption of the patient while being large enough to accommodate a size of the delivery instrument. With a cannula in position in the patient so that there is direct access from outside of the patient to the target site, delivery instrument 100 is then advanced into the patient through the cannula.

Upon positioning of a distal end 144 of elongate housing 142 at the target site, the user may actuate the instrument to cause elongate housing 142 to retract in a proximal direction toward the user, thereby exposing and deploying the implant engagement portion with implant 90 trapped between grippers 112, 120. Outside of elongate housing 142, implant may unfold and otherwise return to its natural shape, which may be a generally flat shape. To the extent any part of the implant does not return to its natural shape, other tools at the surgical site may be used to pull, press or otherwise manipulate the implant for such purpose. Then, while still held by the grippers, implant 90 is anchored to the tissue to perform the repair. Anchorage of the implant may be through the use of staples, sutures, or other similar means. Once the implant is at least partially anchored in a desired manner, delivery instrument 100 is carefully withdrawn from the cannula, leaving the implant in place at the target site. While some force is required to withdraw grippers 112, 120 from the implant, the anchorage of the implant to the tissue prevents the implant from being withdrawn with the instrument as the instrument is removed from the target site. One advantage of delivery instrument 100 is that its small profile, i.e., narrow width, renders it easier to anchor different locations on a periphery of an implant at a target site since a significant portion of the implant is unobstructed. This ensures that it will be possible to apply sufficient anchorage to secure the implant to native tissue prior to withdrawal of the instrument. Prior to complete removal of delivery instrument 100, an optional step may be performed of moving the elongate housing 142 to the extended position after disengagement with the implant. Once final steps in the securement of the implant to the tendon are completed, the cannula is removed and other standard procedures are followed to complete the surgery. Although FIGS. 4 and 5 depict a particular implant 90, it should be appreciated that a variety of implants may be loaded into delivery instrument 100 and other contemplated delivery instrument embodiments, including implants having different sizes. Implants that are used may include or otherwise receive materials such as human collagen, bovine collagen, xenograph collagen, a synthetic material, a polyester material, an absorbable material, an organic material, silk, or combinations thereof.

In another embodiment, delivery instrument 100 is again used to perform a surgical procedure to repair a tendon of the rotator cuff at a target site. This method is similar to the immediately preceding method, with a difference being that the implant is not preloaded in delivery instrument 100. That is, the implant is intraoperatively loaded into the delivery instrument. At the outset of this procedure, at any time prior to inserting delivery instrument 100 into the cannula with access to a target site of the patient, an implant 90 is loaded into delivery instrument. To load the implant, end strip 126 of second gripper 120 may be temporarily moved away from jaw 114 to create a space between the second gripper and the jaw to receive implant 90. Due to the closed loop shape of second gripper, this moving step may be performed in a single user action, as the entire second gripper may be held with one grip. Once implant is slid into place between the second gripper and the jaw, the end strip may be released, and the bias in the second gripper causes the second gripper to press against the implant to provide additional resistance to keep the implant secure between the grippers. From this condition, instrument 100 may be manipulated to cause elongate housing 142 to advance over the implant engagement portion with the first and second grippers holding the implant, as shown in FIGS. 4 and 5, for example, where FIG. 4 shows the instrument in the deployed position and FIG. 5 shows the instrument in the enclosed position. Optionally, prior to manipulating the instrument to arrive at the enclosed position, funnel 150 may be snapped onto a side of the elongate housing as shown in FIG. 4. An inside surface of funnel 150 is concave with a similar shape to an inner surface of elongate housing 142. The use of funnel 150 may case the process of advancing elongate housing 142 over the implant engagement portion by causing at least part of the implant to fold prior to advancing the elongate housing over the implant, as shown in FIG. 4. Once the instrument is in the enclosed position as shown in FIG. 5, the funnel may be removed and the procedure may continue as described above in the preceding embodiment.

In another embodiment, a method of delivering an implant to a surgical site may be performed with delivery instrument 200. Delivery instrument 200 may be used in a method of delivering an implant to a target site as described above with respect to delivery instrument 100, either with a preloaded implant or an intraoperatively loaded implant. When using delivery instrument 200, lateral strips 222, 224 may flex and deform inward into elongate housing 242 when the instrument is moved from the deployed position to the enclosed position so that the lateral strips fit within the lumen of the elongate housing and, conversely, may return to their condition prior to deformation when the instrument is moved from the enclosed position to the deployed position.

In another embodiment, a method of delivering an implant to a surgical site may be performed with delivery instruments 300, 400 and 400'. Delivery instruments 300, 400 and 400' may be used in a method of delivering an implant to a target site as described above with respect to delivery instrument 100, either with a preloaded implant or an intraoperatively loaded implant. When using delivery instrument 300, branches 372, 374, 376, 378 may flex and deform inward into elongate housing 342 when the instrument is moved from the deployed position to the enclosed position to fit within the lumen of the elongate housing. This is shown, for example, through a comparison of delivery instrument 300 in the deployed position in FIG. 8, and in the enclosed position in FIGS. 9 and 10. Conversely, the branches may return to their condition prior to deformation when the instrument is moved from the enclosed position to the deployed position. A similar process of deformation occurs with instruments 400 and 400. This is shown for instrument 400, for example, through a comparison of delivery instrument 400 in the deployed position in FIG. 11, and in the enclosed position in FIGS. 12 and 13. In some variations having a second gripper with a rigid body and a flexible body, the lateral strips of the flexible body may also deform where a maximum width dimension across such lateral strips approaches or exceeds an inner diameter of the elongate housing.

In another embodiment, a method of delivering an implant to a surgical site may be performed with delivery instruments 500, 600. Delivery instruments 500, 600 may be used in a method of delivering an implant to a target site as described above with respect to delivery instrument 100, either with a preloaded implant or an intraoperatively loaded implant. When using delivery instrument 500, wing strips 563, 565 may flex and deform inward into elongate housing 542 when the instrument is moved from the deployed position to the enclosed position to fit within the lumen of the elongate housing. As described elsewhere in the present disclosure, and as with the other contemplated embodiments, a funnel 550 may also be used to direct a deformation of the wing strips while the instrument is in the deployed position to case the process of moving elongate housing 542 to the extended position to enclose the grippers and the wing strips. Conversely, the wing strips may return to their condition prior to deformation when the instrument is moved from the enclosed position to the deployed position. Wing strips 623, 625 of delivery instrument 600 may perform in a similar manner to the wing strips of delivery instrument 500, as described above.

In another embodiment, a method of delivering an implant to a surgical site may be performed with delivery instrument 700. Delivery instrument 700 may be used in a method of delivering an implant to a target site as described above with respect to delivery instrument 100, either with a preloaded implant or an intraoperatively loaded implant. Differences in the use of delivery instrument 700 compared to instrument 100 include the following. To load an implant onto delivery instrument 700, actuators, in the depicted embodiment slidable blocks 771, 772, are slid to a gripper-deployment position. In such position, outer shaft 770 is retracted exposing the grippers, first gripper 712 and second gripper 720 being spaced apart. From this position, an implant such as implant 90, may be loaded between grippers 712, 720, as shown in FIGS. 24A and 24B. Then, to prepare delivery instrument 700 for insertion through the surgical cannula to deliver to a target site, block 771 on handle 775 is slid into the locked position to bring first gripper 712 and second gripper closer together 720, as shown in FIG. 25, thereby clamping the implant. Once the implant is clamped, block 772 on handle 775 is slid into the gripper-enclosure position to advance outer shaft 770 over the grippers, causing the prongs of grippers 712, 720 to move laterally inward to fit within the distally advancing outer shaft 770, as shown in FIGS. 26A and 26B. Now, delivery instrument 700 appears as shown in FIG. 21 and is ready to be directed to the target site via the surgical cannula. The same process may be performed in reverse to release the implant at the target site. A user may use discretion as to whether to release the implant from the instrument before anchoring the implant in place since delivery instrument 700 is capable of doing so prior to anchoring the implant.

The above method of using delivery instrument 700 may also be performed with the variations of delivery instrument 700 described in the present application disclosure. In some examples of these variations, the prongs of the first gripper and the second gripper may respond differently when block 772 on handle 775 is slid into the gripper-enclosure position. For instance, in some examples, when block 772 on handle 775 is slid into the gripper-enclosure position, the prongs of second gripper 720 move laterally inward to fit within the distally advancing outer shaft 770 while the prongs of first gripper 712 remain static and unchanged. In some examples, when block 772 on handle 775 is slid into the gripper-enclosure position, the prongs of first gripper 712 move laterally inward to fit within the distally advancing outer shaft 770 while the prongs of second gripper 720 remain static and unchanged. In still further examples, when block 772 on handle 775 is slid into the gripper-enclosure position, the prongs of first gripper 712 and second gripper 720 both remain static and unchanged. The same principles apply in reverse when the outer shaft 770 is retracted to expose the first and second grippers.

Delivery instruments 700A, 700B, 700C, 700D, 700E, 700F, 700G may also be used in a method of delivering an implant to a surgical site in a similar manner to that described for delivery instrument 700. When using delivery instruments 700A-700D, an additional step may be taken prior to loading an implant into the instrument by manipulating an additional actuation mechanism of the instrument to adjust a lateral spacing of the prongs, as shown for example in FIGS. 27 and 28, a depth spacing between the grippers, as shown for example in FIGS. 29 and 30, or both when the instrument is so equipped, to accommodate a particular size of implant being loaded onto the instrument. When using delivery instrument 700G, a user may determine based on a particular implant to be implanted or based on other circumstances of a surgery that the gripping features on the instrument should be substituted with other gripping features. Where various modular components are available with different gripping features, adapter 781G may be detached from central shaft 710G to remove the current modular component and replace it with another modular component with the desired gripping features.

Figure 47:
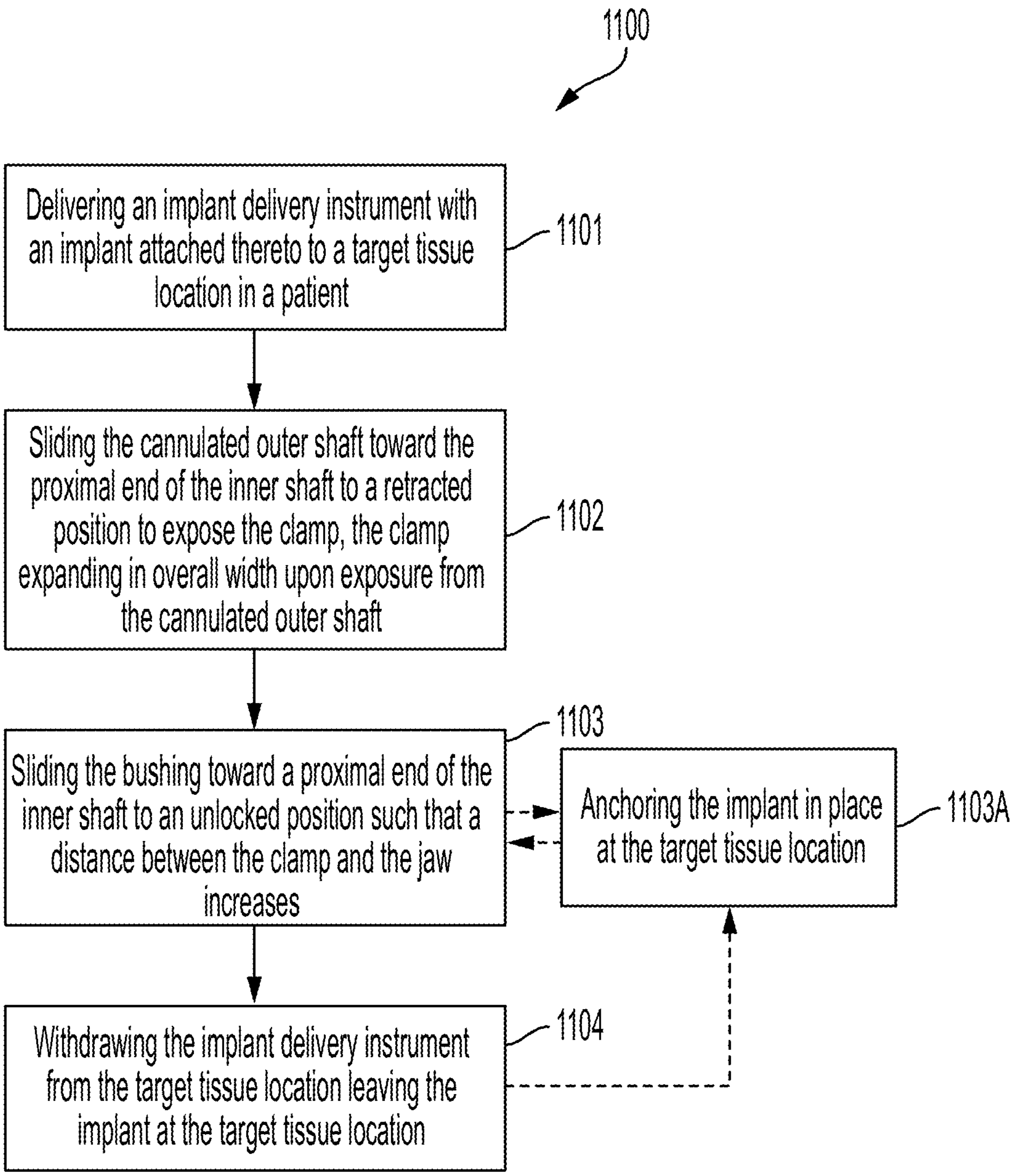
FIG. 47 is a flow chart illustrating a method of delivering an implant to a surgical site according to one embodiment of the disclosure.

In one embodiment, a method 1100 of delivering an implant to a surgical site may proceed according to one or more of the following steps as shown in FIG. 47. This method may be performed using implant delivery instrument 700, for example. An exemplary implant delivery instrument used in this embodiment includes an inner shaft, a bushing, a clamp, a jaw and a cannulated outer shaft. The bushing is slidably disposed over the inner shaft such that the bushing is axially translatable along a central longitudinal axis of the inner shaft. The clamp and the jaw extend distally from a distal portion of the inner shaft. The cannulated outer shaft is disposed over the inner shaft and the bushing such that the cannulated outer shaft is axially translatable along the central longitudinal axis. Step 1101 includes delivering an implant delivery instrument with an implant attached thereto to a target tissue location in a patient. Step 1102 includes sliding the cannulated outer shaft toward the proximal end of the inner shaft to a retracted position to expose the clamp, the clamp expanding in overall width upon exposure from the cannulated outer shaft. Step 1103 includes sliding the bushing toward a proximal end of the inner shaft to an unlocked position such that a distance between the clamp and the jaw increases. In some examples, a step 1103A may be performed that includes anchoring the implant in place at the target tissue location. Step 1104 includes withdrawing the implant delivery instrument from the target tissue location leaving the implant at the target tissue location. Step 1103A may be performed prior to the withdrawing step.

In another embodiment, a method of delivering an implant to a surgical site may be performed with delivery instruments 800 and 900. Delivery instruments 800, 900 may be used in a method of delivering an implant to a target site as described above with respect to delivery instrument 100, either with a preloaded implant or an intraoperatively loaded implant. A preloaded delivery instrument may include a pre-packaged graft while an intraoperatively loaded delivery instrument may be used in conjunction with any number of compatible implants available at the time of surgery. Differences in the use of delivery instruments 800, 900 compared to instrument 100 include the method steps and operational features described below. While the below description refers specifically to delivery instrument 800, it should be appreciated that the features described for delivery instrument 800 are equally applicable to delivery instrument 900.

To load an implant onto delivery instrument 800, a first control (not shown) for outer shaft 870 is moved to the retracted position and a second control (not shown) for bushing 842 is moved to the unlocked position, as shown in FIG. 35A. From this position, an implant 90 may be deposited in between first gripper 812 and second gripper 820. To the extent lateral wings 862, 864 are in an expanded state at this juncture, a third control (not shown) may be moved to bring the lateral wings closer to central axis 801 of the instrument, as shown in FIG. 35B. Once implant 90 is loaded onto the grippers, second control is moved to the locked position to close first and second gripper 812, 820 together, as shown in FIG. 36A. Then, first control is moved from the gripper-deployment position to the gripper-enclosure position, advancing outer shaft 870 over and enclosing the grippers and the implant. From this position, delivery instrument 800 may be advanced through a surgical cannula to a target site of a patient.

With continued reference to delivery instrument 800, to deposit implant at the target site of the patient once the instrument is positioned at the target site, the first control is moved from the gripper-enclosure position to the gripper-deployment position to expose implant 90. At this time, implant 90 is still being clamped by the grippers. Although implant should expand once outer shaft 870 is withdrawn, third control may be used to advance the central wing shaft, causing lateral wings 862, 864 to buckle and expand laterally, as shown in FIG. 36B, to spread the implant out at the target site. Surfaces of the lateral wings serve to push out any wrinkles in the implant in order to minimize any surface area lost when the implant was crimpled within the outer shaft. Then, second control is moved from the locked position to the unlocked position to release the implant from the instrument. Either before, during, or after releasing the implant from the grippers, the implant may be anchored to the tissue to be repaired. This completes the implant placement process. Prior to removing delivery instrument 800 from the site, lateral wings are once again drawn close to central axis 801 via the third control, grippers 812, 820 are locked via the second control, and outer shaft 870 is advanced over the grippers via the first control.

Figure 39:
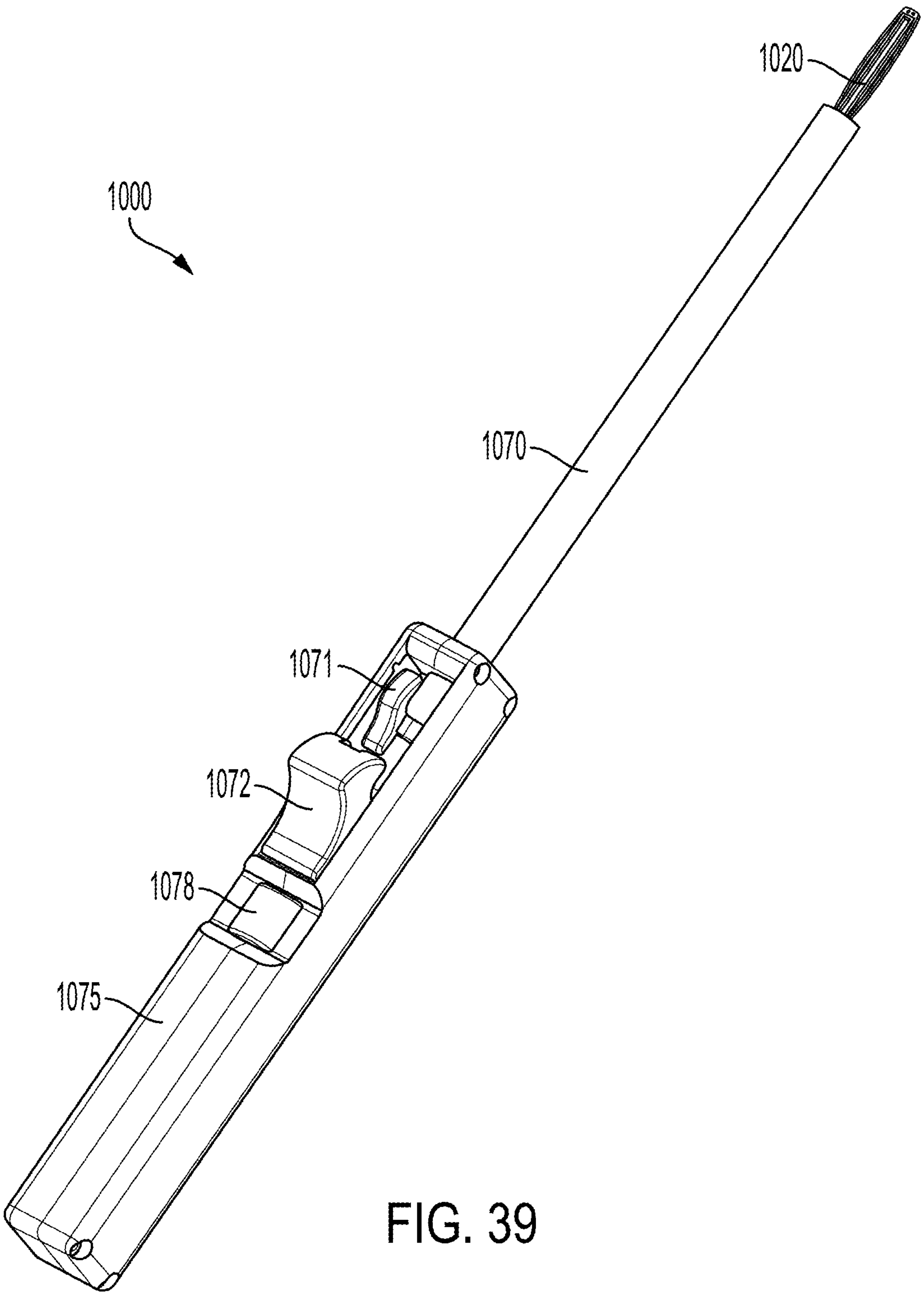
FIGS. 39-46 are various views of a delivery instrument according to one embodiment of the disclosure.
Figure 40:
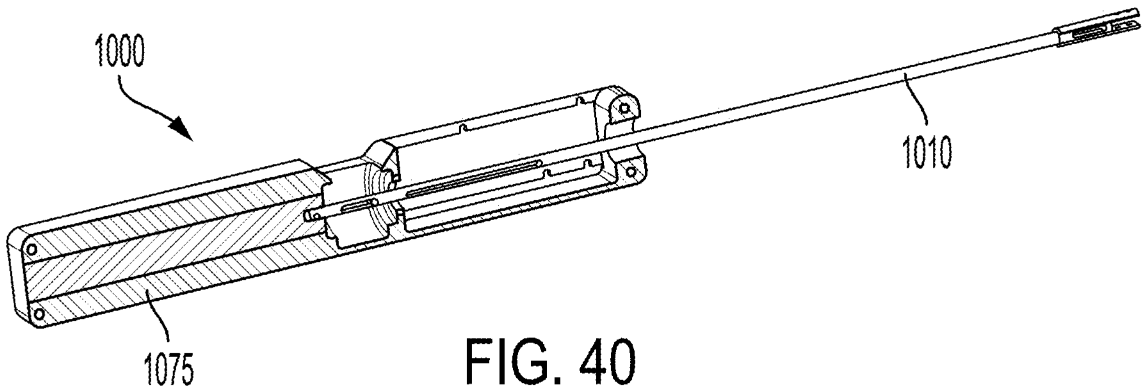
Figure 41:
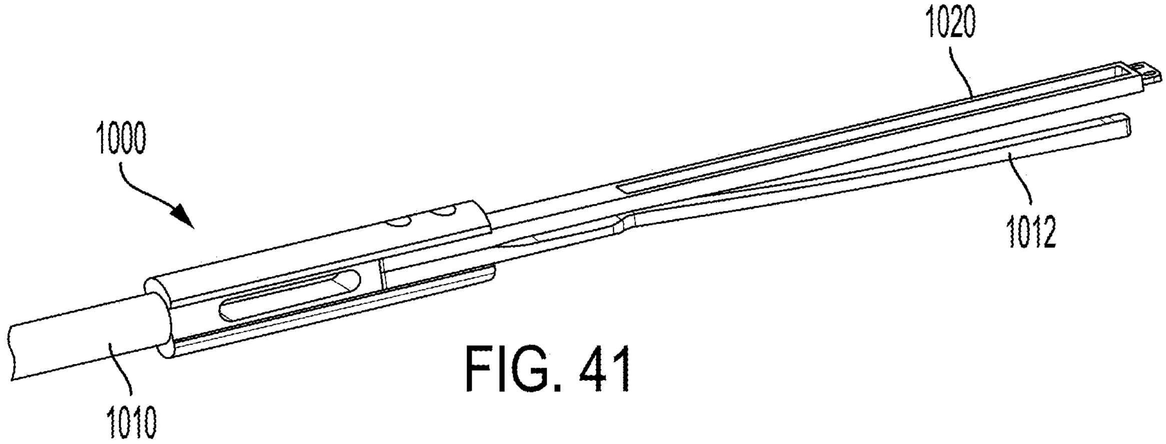
Figure 42:
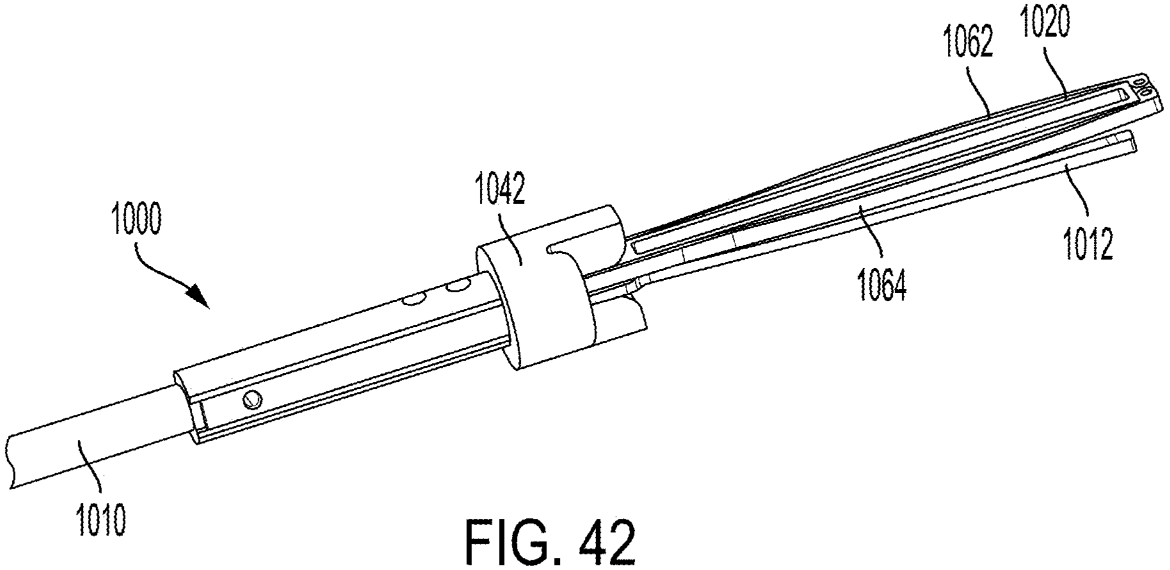
Figure 43:
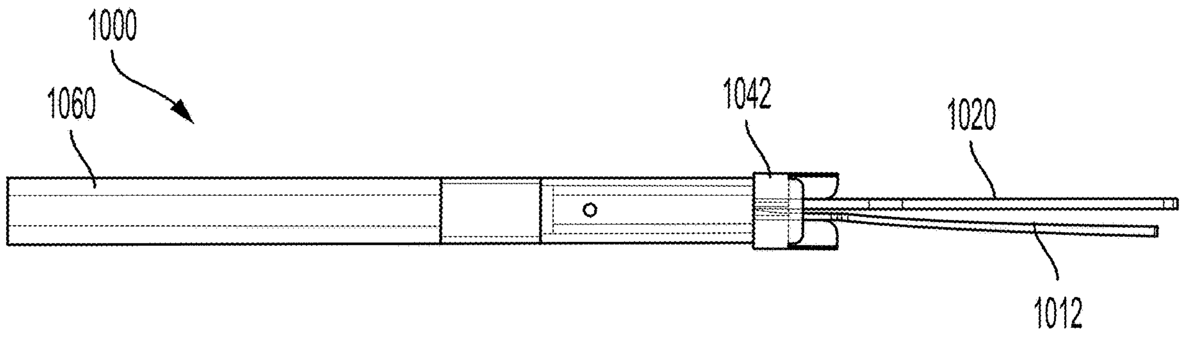
Figure 44:
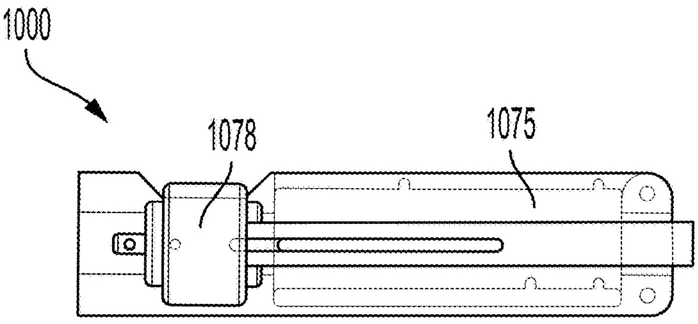
Figure 45:
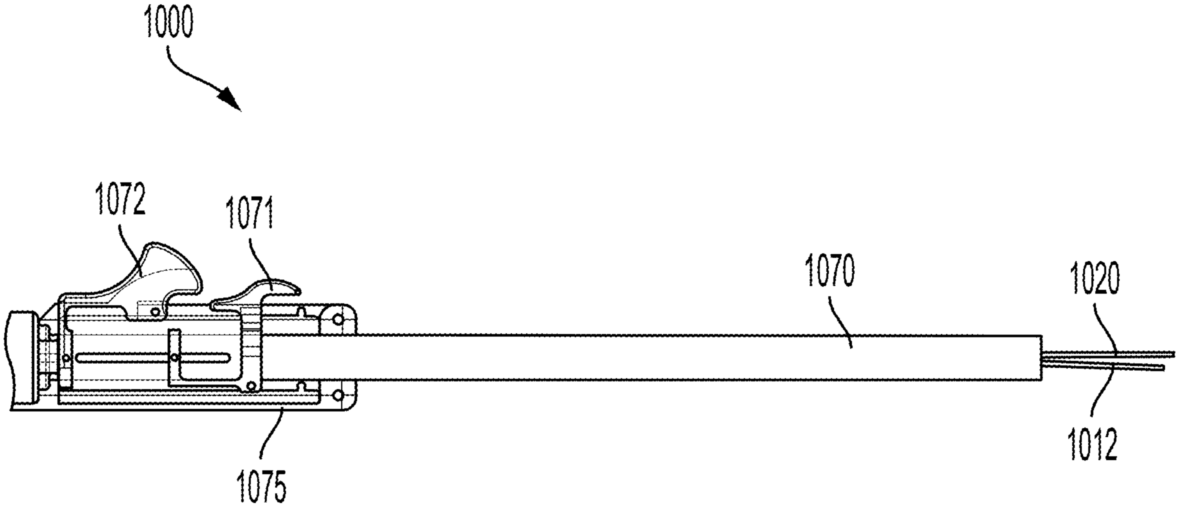
Figure 46:
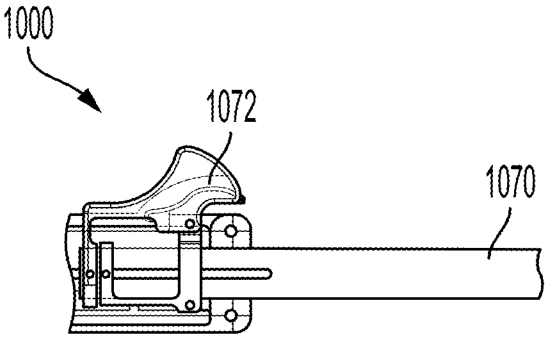

In another embodiment, a method of delivering an implant to a surgical site may be performed with delivery instrument 1000, shown in FIG. 39 for example. Delivery instrument 1000 may be used in a method of delivering an implant to a target site as described above with respect to delivery instrument 100, either with a preloaded implant or an intraoperatively loaded implant. Operation of delivery instrument 1000 may also be generally as described for delivery instrument 800, operable with specific user controls provided in delivery instrument 1000. These controls include control buttons 1071, 1072 and thumb wheel control 1078.

Figure 48:
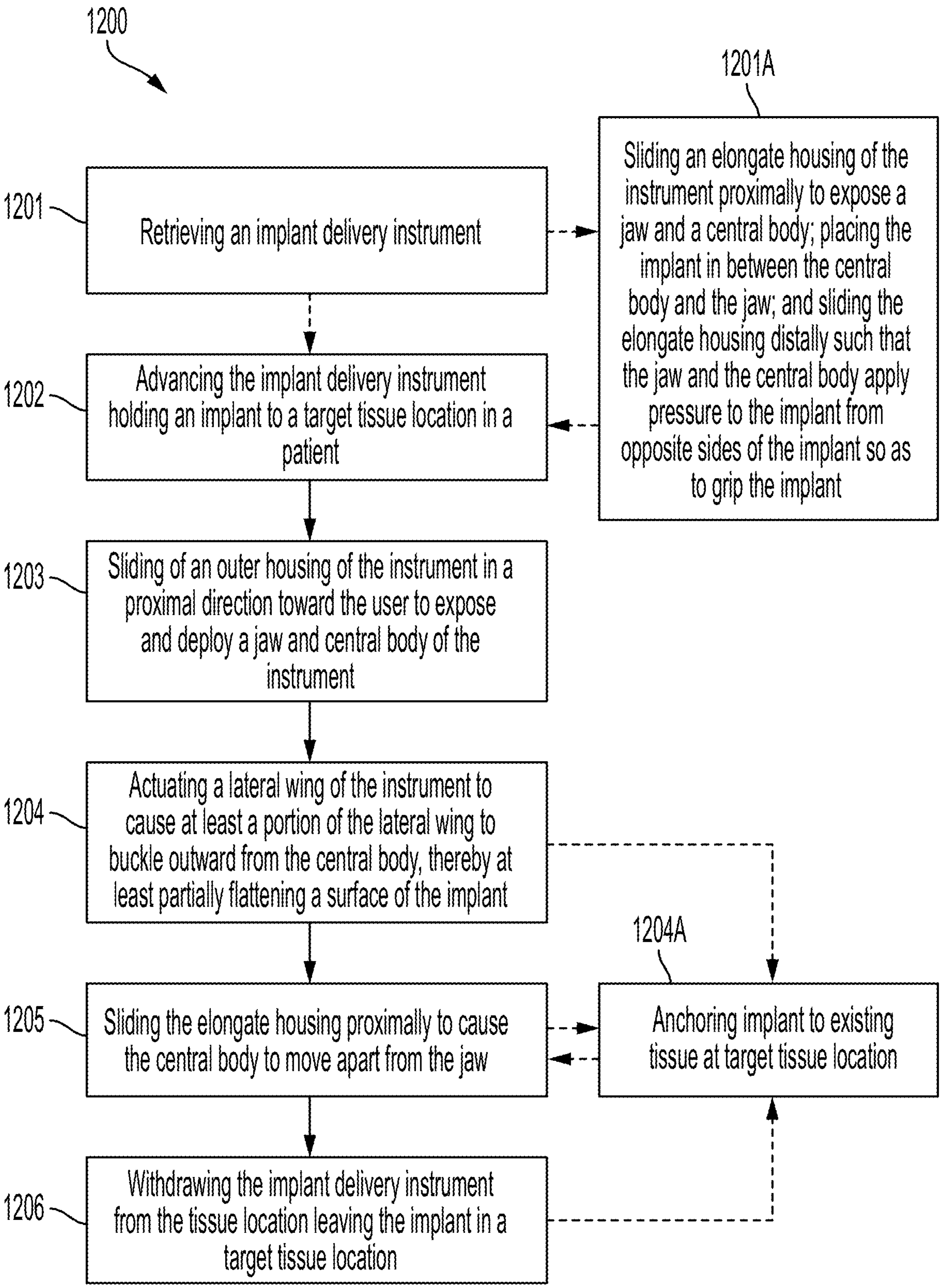
FIG. 48 is a flow chart illustrating a method of delivering an implant to a surgical site according to one embodiment of the disclosure.

In yet another embodiment, a method 1200 of delivering an implant to a surgical site may proceed according to one or more of the following steps as shown in FIG. 48. Step 1201 includes retrieving an implant delivery instrument. In one example, the implant delivery instrument includes a base shaft, a first actuation assembly, a second actuation assembly and a third actuation assembly. The base extends along a central longitudinal axis in a proximal-distal direction and includes a jaw and a central body extending from a distal end thereof. The first actuation assembly includes a lateral wing operatively connected to the central body, the central body being aligned with the central longitudinal axis. The second actuation assembly includes an elongate housing with a lumen therethrough, the base shaft being disposed within the lumen and the elongate housing being slidable along the base shaft. The third actuation assembly includes an outer housing that is slidably disposed over the base shaft. In other examples, the implant delivery instrument may be instrument 800, 900, 1000, or other similar delivery instruments. In some examples, the delivery instrument may already be holding an implant. In other examples, the method may include, prior to the advancing step discussed below, step 1201A including sliding the elongate housing proximally to expose the jaw and the central body; placing the implant in between the central body and the jaw; and sliding the elongate housing distally such that the jaw and the central body apply pressure to the implant from opposite sides of the implant to grip the implant.

With the instrument ready for use, step 1202 includes advancing the implant delivery instrument holding an implant to a tissue location in a patient. In some variations of this embodiment, the method may begin at step 1202. At step 1203, sliding of the outer housing in a proximal direction toward the user exposes and deploys the jaw and the central body. At step 1204, actuating the lateral wing causes at least a portion of the lateral wing to buckle outward from the central body, thereby at least partially flattening a surface of the implant. At step 1205, sliding the elongate housing proximally causes the central body to move apart from the jaw. At step 1206, withdrawing the implant delivery instrument from the tissue location leaves the implant in the tissue location for the implant to function to repair the target tissue.

In some variations of the method 1200, the method may also include step 1204A, a step of anchoring the implant to a portion of tissue at the tissue location. Such anchoring may be performed before or after withdrawing the implant delivery instrument.

In some embodiments, a method of delivering an implant may be performed with the use of any one of delivery instruments 1300, 1400, 1500. Methods using such delivery instruments may be as described above with respect to delivery instrument 300, either with a preloaded implant or an intraoperatively loaded implant. When using delivery instrument 1300, 1400, 1500, the branches may flex and deform inward into the elongate housing of the delivery instrument when the instrument is moved from the deployed position to the enclosed position to fit within the lumen of the elongate housing. Conversely, the branches may return to their condition prior to deformation when the instrument is moved from the enclosed position to the deployed position. To detach implant 90 from delivery instrument 1300, 1400, 1500, the prongs of gripper 1320, 1420, 1520 are pulled through implant 90, e.g., through openings in implant 90. In some variations, implant 90 may be anchored to tissue in the patient before detachment of delivery instrument 1300, 1400, 1500 to hold implant 90 in place during detachment of implant 90. In other variations, a secondary instrument may be used to hold implant 90 in place within the patient while gripper 1320, 1420, 1520 is withdrawn.

Although the invention herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. An implant delivery instrument comprising:

an inner shaft including a distal portion;

a bushing slidably disposed over the inner shaft such that the bushing is axially translatable along a central longitudinal axis of the inner shaft;

a clamp extending distally from the distal portion and a jaw extending distally from the distal portion; and a cannulated outer shaft disposed over the inner shaft and the bushing such that the cannulated outer shaft is axially translatable along the central longitudinal axis, wherein the bushing is translatable between an unlocked position where the clamp is spaced apart from the jaw by a first distance and a locked position where the clamp is spaced apart from the jaw by a second distance less than the first distance, wherein the cannulated outer shaft is translatable between a retracted position where the clamp has a first maximum lateral dimension and an extended position where the clamp has a second maximum lateral dimension less than the first maximum lateral dimension, and wherein when the cannulated outer shaft is in the retracted position, the clamp has the first maximum lateral dimension when the bushing is in the locked position and when the bushing is in the unlocked position.

2. The implant delivery instrument of claim 1, wherein the clamp further comprises three prongs arranged to pass through a first plane.

3. The implant delivery instrument of claim 2, wherein when the cannulated outer shaft is in the retracted position, the three prongs are spaced apart from each other by a third maximum lateral dimension and when the cannulated outer shaft is in the extended position, the three prongs are spaced apart from each other by a fourth maximum lateral dimension less than the third maximum lateral dimension.

4. The implant delivery instrument of claim 1, wherein the clamp further comprises a plurality of prongs.

5. The implant delivery instrument of claim 4, further comprising an actuation mechanism configured to control a spacing of the plurality of prongs while the cannulated outer shaft is in the retracted position.

6. The implant delivery instrument of claim 1, wherein the jaw is a single jaw that is immovable with respect to the inner shaft.

7. The implant delivery instrument of claim 1, further comprising a first actuation mechanism configured to axially translate the bushing and a second actuation mechanism configured to axially translate the cannulated outer shaft.

8. An implant delivery system comprising:

an implant; and an implant delivery instrument comprising:

an inner shaft including a distal portion;

a bushing slidably disposed over the inner shaft such that the bushing is axially translatable along a central longitudinal axis of the inner shaft;

a clamp extending distally from the distal portion and a jaw extending distally from the distal portion;

a cannulated outer shaft disposed over the inner shaft and the bushing such that the cannulated outer shaft is axially translatable along the central longitudinal axis;

a first actuation mechanism configured to translate the bushing between an unlocked position where the clamp is spaced apart from the jaw by a first distance and a locked position where the clamp is spaced apart from the jaw by a second distance less than the first distance, and a second actuation mechanism configured to translate the cannulated outer shaft between a retracted position where the clamp has a first maximum lateral dimension and an extended position where the clamp has a second maximum lateral dimension less than the first maximum lateral dimension.

9. The implant delivery system of claim 8, wherein the clamp further comprises a plurality of prongs.

10. The implant delivery system of claim 9, wherein when the cannulated outer shaft is in the retracted position, the plurality of prongs are spaced apart from each other by a third maximum lateral dimension and when the cannulated outer shaft is in the extended position, the plurality of prongs are spaced apart from each other by a fourth maximum lateral dimension less than the third maximum lateral dimension.

11. The implant delivery system of claim 8, wherein the jaw is a single jaw that is immovable with respect to the inner shaft.

12. The implant delivery system of claim 8, wherein when the cannulated outer shaft translates from the retracted to the extended position, a width of the jaw remains unchanged.

13. The implant delivery system of claim 8, wherein at least one of the clamp and the jaw include gripping protrusions.

14. A method of positioning an implant in a patient comprising:

delivering an implant delivery instrument with an implant attached thereto to a target tissue location in a patient, the implant delivery instrument comprising:

an inner shaft including a distal portion;

a bushing slidably disposed over the inner shaft such that the bushing is axially translatable along a central longitudinal axis of the inner shaft;

a clamp extending distally from the distal portion and a jaw extending distally from the distal portion, wherein the implant is positioned between the clamp and the jaw; and a cannulated outer shaft disposed over the inner shaft and the bushing such that the cannulated outer shaft is axially translatable along the central longitudinal axis;

sliding the cannulated outer shaft toward a proximal end of the inner shaft to a retracted position to expose the clamp and the implant, the clamp expanding in overall width upon exposure from the cannulated outer shaft;

sliding the bushing toward the proximal end of the inner shaft to an unlocked position such that a distance between the clamp and the jaw increases; and withdrawing the implant delivery instrument from the target tissue location leaving the implant at the target tissue location.

15. The method of claim 14, further comprising anchoring the implant in place at the target tissue location prior to withdrawing the implant delivery instrument.

16. The method of claim 14, wherein sliding the bushing toward the proximal end of the inner shaft to the unlocked position occurs after sliding the cannulated outer shaft toward the proximal end of the inner shaft such that prior to sliding the bushing, the clamp and the jaw hold the implant and the implant is exposed from the cannulated outer shaft.

17. The method of claim 14, wherein sliding the cannulated outer shaft toward the proximal end of the inner shaft causes a plurality of prongs of the clamp to spread apart relative to each other.

18. The method of claim 14, further comprising, prior to delivering the implant delivery instrument, adjusting a spacing between a plurality of prongs of the clamp while the clamp is exposed from the cannulated outer shaft.

19. The method of claim 14, wherein sliding the bushing toward the proximal end of the inner shaft to the unlocked position causes the clamp to move away from the jaw, a position of the jaw relative to the inner shaft remaining unchanged based on the sliding of the bushing.

20. The method of claim 14, wherein sliding the bushing toward the proximal end of the inner shaft to the unlocked position causes a width of the jaw to remain unchanged.

* * * * *